US010184012B2

(12) United States Patent
Bae et al.

(10) Patent No.: US 10,184,012 B2
(45) Date of Patent: Jan. 22, 2019

(54) MODIFIED BUTADIENE-BASED POLYMER AND MODIFIER USEFUL FOR PREPARING THE SAME

(71) Applicant: LG Chem, Ltd., Seoul (KR)

(72) Inventors: Hyo Jin Bae, Daejeon (KR); Won Hee Kim, Daejeon (KR); Hee Jung Jeon, Daejeon (KR); Seung Ho Choi, Daejeon (KR); Kyoung Hwan Oh, Daejeon (KR); Dong Hui Kim, Daejeon (KR); Hyun Woong Park, Daejeon (KR); Won Mun Choi, Daejeon (KR); Jeong Heon Ahn, Daejeon (KR); Suk Youn Kang, Daejeon (KR)

(73) Assignee: LG Chem, Ltd. (KR)

( * ) Notice: Subject to any disclaimer, the term of this patent is extended or adjusted under 35 U.S.C. 154(b) by 56 days.

(21) Appl. No.: 15/505,371

(22) PCT Filed: Nov. 27, 2015

(86) PCT No.: PCT/KR2015/012818
§ 371 (c)(1),
(2) Date: Feb. 21, 2017

(87) PCT Pub. No.: WO2016/085283
PCT Pub. Date: Jun. 2, 2016

(65) Prior Publication Data
US 2017/0275390 A1 Sep. 28, 2017

(30) Foreign Application Priority Data

Nov. 28, 2014 (KR) .................. 10-2014-0168978
Dec. 4, 2014 (KR) .................. 10-2014-0172962
Dec. 22, 2014 (KR) .................. 10-2014-0186009
Nov. 26, 2015 (KR) .................. 10-2015-0166682

(51) Int. Cl.
C08C 19/25 (2006.01)
C07F 7/18 (2006.01)
C08F 236/10 (2006.01)
B60C 1/00 (2006.01)
C08F 36/04 (2006.01)
C08C 19/22 (2006.01)
C08C 19/26 (2006.01)
C08F 212/08 (2006.01)
C08F 4/46 (2006.01)
C08F 4/48 (2006.01)
C08F 236/06 (2006.01)
C08K 3/04 (2006.01)
C08K 3/36 (2006.01)
C08L 9/00 (2006.01)
C08L 9/06 (2006.01)
C08L 15/00 (2006.01)

(52) U.S. Cl.
CPC ................ *C08C 19/25* (2013.01); *B60C 1/00* (2013.01); *C07F 7/1804* (2013.01); *C08C 19/22* (2013.01); *C08C 19/26* (2013.01); *C08F 4/46* (2013.01); *C08F 4/48* (2013.01); *C08F 36/04* (2013.01); *C08F 212/08* (2013.01); *C08F 236/06* (2013.01); *C08F 236/10* (2013.01); *C08K 3/04* (2013.01); *C08K 3/36* (2013.01); *C08L 9/00* (2013.01); *C08L 9/06* (2013.01); *C08L 15/00* (2013.01)

(58) Field of Classification Search
None
See application file for complete search history.

(56) References Cited

U.S. PATENT DOCUMENTS

| 4,239,539 | A | 12/1980 | Ginsberg et al. |
|---|---|---|---|
| 4,330,444 | A | 5/1982 | Pollman |
| 5,532,398 | A | 7/1996 | Wolter et al. |
| 5,948,927 | A | 9/1999 | Gunther et al. |
| 6,228,496 | B1 | 5/2001 | Lawton et al. |
| 2004/0167275 | A1 | 8/2004 | Okuhira et al. |
| 2004/0254301 | A1 | 12/2004 | Tsukimawashi et al. |
| 2005/0288415 | A1 | 12/2005 | Beers et al. |
| 2012/0059121 | A1 | 3/2012 | Backer et al. |
| 2013/0302627 | A1 | 11/2013 | Roehrig et al. |
| 2013/0323519 | A1 | 12/2013 | Klun et al. |
| 2014/0243476 | A1 | 8/2014 | Lee et al. |
| 2014/0296421 | A1 | 10/2014 | Miyazaki |
| 2014/0309370 | A1 | 10/2014 | Ostendorf et al. |
| 2015/0221886 | A1 | 8/2015 | Klun et al. |
| 2017/0066850 | A1 | 3/2017 | Lee et al. |

FOREIGN PATENT DOCUMENTS

| CN | 104072816 A | 10/2014 |
|---|---|---|
| JP | H0657767 B2 | 8/1994 |
| JP | 2004210977 A | 7/2004 |

(Continued)

OTHER PUBLICATIONS

International Search Report from PCT/KR2015/012821, dated Mar. 22, 2016.

(Continued)

*Primary Examiner* — Robert S Loewe
(74) *Attorney, Agent, or Firm* — Lerner, David, Littenberg, Krumholz & Mentlik, LLP

(57) ABSTRACT

The present invention provides a modified butadiene-based polymer capable of enhancing dispersability of an inorganic filler when used in a rubber composition, and enhancing viscoelasticity, a tensile property and processibility of the rubber composition in a balanced way from an interaction with the inorganic filler, and a modifier useful for preparing the same.

19 Claims, No Drawings

(56) References Cited

FOREIGN PATENT DOCUMENTS

| | | | |
|---|---|---|---|
| JP | 4176486 | B2 | 11/2008 |
| JP | 2013060525 | A | 4/2013 |
| JP | 2013082842 | A | 5/2013 |
| JP | 2013087210 | A | 5/2013 |
| JP | 2013087219 | A | 5/2013 |
| JP | 2014177517 | A | 9/2014 |
| JP | 2014177520 | A | 9/2014 |
| JP | 2014189774 | A | 10/2014 |
| JP | 2014534291 | A | 12/2014 |
| JP | 2015529580 | A | 10/2015 |
| JP | 2016014122 | A | 1/2016 |
| KR | 20130090811 | A | 8/2013 |
| KR | 20140122664 | A | 10/2014 |
| WO | 03029299 | A1 | 4/2003 |
| WO | 2012078469 | A1 | 6/2012 |
| WO | 2012106184 | A2 | 8/2012 |
| WO | 2014025348 | A1 | 2/2014 |

OTHER PUBLICATIONS

International Search Report from PCT/KR2015/012818, dated Mar. 23, 2016.
Extended European Search Report for Application No. EP15863701.7 dated Nov. 7, 2017.
Database WPI, Week 201325, Thomson Scientific, London, GB; AN 2013-E55395, XP002774672, 2017 Clarivate Analytics.
Database WPI, Week 201334, Thomson Scientific, London, GB; AN 2013-H12432, XP002774673, 2017 Clarivate Analytics.
Database WPI, Week 201335, Thomson Scientific, London, GB; AN 2013-H12439, XP002774674, 2017 Clarivate Analytics.
Database WPI, Week 201325, Thomson Scientific, London, GB; AN 2013-555395, XP002774695, 2017 Clarivate Analytics.
Database WPI, Week 201334, Thomson Scientific, London, GB; AN 2013-H12432, XP002774696, 2017 Clarivate Analytics.
Database WPI, Week 201335, Thomson Scientific, London, GB; AN 2013-H12439, XP002774697, 2017 Clarivate Analytics.
Extended European Search Report for Application No. EP15864093.8 dated Nov. 7, 2017.
Chinese Search Report for CN2015800480694 dated Jun. 4, 2018.
Eren, T. et al., Polymerization of Methacryl and Triethoxysilane Functionalized Stearate Ester: Titanium Dioxide Composite Films and Their Photocatalytic Degradations, Journal Of Applied Polymer Science, Aug. 5, 2007, vol. 105, No. 3, pp. 1426-1436, XP055516029.
Schmider, M. et al., "A Versatile Synthetic Route to Phosphonate-Functional Monomers, Oligomers, Silanes, and Hybrid Nanoparticles", Macromolecules, Nov. 1, 2005, vol. 38, No. 23, pp. 9548-9555., XP055515524.

MODIFIED BUTADIENE-BASED POLYMER AND MODIFIER USEFUL FOR PREPARING THE SAME

CROSS-REFERENCE TO RELATED APPLICATIONS

This application is a national phase entry under 35 U.S.C. § 371 of International Application No. PCT/KR2015/012818, filed Nov. 27, 2015, which claims priority to Korean Patent Application No. 10-2014-0168978, filed with the Korean Intellectual Property Office on Nov. 28, 2014, Korean Patent Application No. 10-2014-0172962, filed with the Korean Intellectual Property Office on Dec. 4, 2014, Korean Patent Application No. 10-2014-0186009, filed with the Korean Intellectual Property Office on Dec. 22, 2014, and Korean Patent Application No. 10-2015-0166682, filed with the Korean Intellectual Property Office on Nov. 26, 2015, the entire contents of which are incorporated herein by reference.

FIELD OF THE INVENTION

This application claims priority to and the benefits of Korean Patent Application No. 10-2014-0168978 filed with the Korean Intellectual Property Office on Nov. 28, 2014, Korean Patent Application No. 10-2014-0172962 filed with the Korean Intellectual Property Office on Dec. 4, 2014, Korean Patent Application No. 10-2014-0186009 filed with the Korean Intellectual Property Office on Dec. 22, 2014, and Korean Patent Application No. 10-2015-0166682, filed with the Korean Intellectual Property Office on Nov. 26, 2015, the entire contents of which are incorporated herein by reference.

The present invention relates to a modified butadiene-based polymer and a modifier useful for preparing the same.

DESCRIPTION OF THE RELATED ART

In order to obtain a rubber composition having a low heating property, mixing an inorganic filler such as silica or carbon black to a rubber polymer has been noramlly used. However, interaction between a rubber polymer and an inorganic filler is usually very weak, and there has been problems in that the inorganic filler, particularly silica, is difficult to be dispersed in a rubber composition, and processing is difficult due to high torque loaded during a mixing process.

In view of the above, a method of using a modified polymer for silica containing a functional group interacting with a silane coupling agent or silica to increase affinity for silica has been proposed. As one example, a modified conjugated diene-based polymer in which a polymerization active end of a conjugated diene-based polymer obtained from anion polymerizing a conjugated diene monomer using an organic lithium compound as a polymerization initiator is modified to an alkoxysilane derivative containing a functional group intracting with a filler has been proposed.

However, in the case of a rubber composition using a modified conjugated diene-based polymer prepared through the above-mentioned method, a low heating property may be secured by mixing a reinforcing filler thereto, however, there is a problem in that abrasion resistance greatly declines.

With recent increasing demands for high fuel efficiency, development of a rubber composition increasing abrasion resistance in a balanced way together with high fuel efficiency performance improved from a heating property decline caused by a rolling resistance decrease in tires.

DISCLOSURE OF THE INVENTION

Technical Problem

An object of the present invention is to provide a modified butadiene-based polymer exhibiting dispersability as well as excellent affinity for an inorganic filler when used in a rubber composition, and thereby capable of improving viscoelasticity, a tensile property and processibility of the rubber composition in a balanced way.

Another object of the present invention is to provide a modified butadiene-based polymer prepared using a modifier.

Another object of the present invention is to provide a rubber composition and a molded rubber article including the modified butadiene-based polymer.

Another object of the present invention is to provide a modifier useful for preparing the modified butadiene-based polymer.

Technical Solution

In view of the above, one embodiment of the present invention provides a modified butadiene-based polymer including a modifier-derived functional group of the following Chemical Formula 1 as a modified polymer of a lanthanide rare earth element-catalyzed butadiene-based polymer:

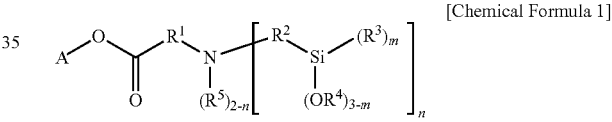

[Chemical Formula 1]

in Chemical Formula 1,

A is a hydrocarbon group having 1 to 20 carbon atoms, or a hydrocarbon group having 1 to 20 carbon atoms including one or more heteroatoms selected from the group consisting of N, S and O, $R^1$ and $R^2$ are each independently a divalent hydrocarbon group having 1 to 20 carbon atoms unsubstituted or subsituted with one or more substituents selected from the group consisting of a linear or branched alkyl group having 1 to 20 carbon atoms, a cycloalkyl group having 3 to carbon atoms and an aryl group having 6 to 30 carbon atoms, $R^3$ to $R^5$ are each independently a monovalent hydrocarbon group having 1 to 20 carbon atoms, m is an integer of 0 to 3, and n is an integer of 1 or 2, but when A is a hydrocarbon group having 1 to 20 carbon atoms, n is an integer of 2.

Another embodiment of the present invention provides a method for preparing the modified butadiene-based polymer including modifying by reacting a butadiene-based polymer having a lanthanide rare earth element-catalyzed active organic metal site with the modifier of Chemical Formula 1.

Another embodiment of the present invention provides a rubber composition including the modified butadiene-based polymer, and a molded rubber article and a tire manufactured using the same.

Another embodiment of the present invention provides the modifier of Chemical Formula 1 useful for preparing the modified butadiene-based polymer.

Another embodiment of the present invention provides a method for preparing the modifier of Chemical Formula 1 including reacting a compound of the following Chemical Formula 2 and a compound of the following Chemical Formula 3:

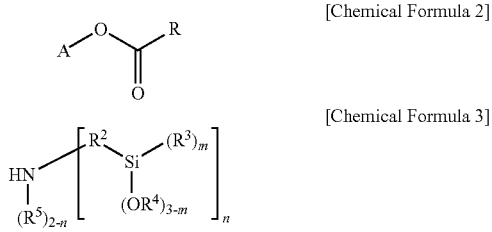

[Chemical Formula 2]

[Chemical Formula 3]

in Chemical Formulae 2 and 3,

A is a hydrocarbon group having 1 to 20 carbon atoms, or a hydrocarbon group having 1 to 20 carbon atoms including one or more heteroatoms selected from the group consisting of N, S and O, R is an alkenyl group having 2 to 20 carbon atoms unsubstituted or subsituted with one or more substituents selected from the group consisting of a linear or branched alkyl group having 1 to 20 carbon atoms, a cycloalkyl group having 3 to 20 carbon atoms and an aryl group having 6 to 30 carbon atoms, $R^2$ is a divalent hydrocarbon group having 1 to 20 carbon atoms unsubstituted or subsituted with one or more substituents selected from the group consisting of a linear or branched alkyl group having 1 to 20 carbon atoms, a cycloalkyl group having 3 to 20 carbon atoms and an aryl group having 6 to 30 carbon atoms, $R^3$ to $R^5$ are each independently a monovalent hydrocarbon group having 1 to 20 carbon atoms, m is an integer of 0 to 3, and n is an integer of 1 or 2, but when A is a hydrocarbon group having 1 to 20 carbon atoms, n is an integer of 2.

Other specifics of the embodiments of the present invention are included in the detailed descriptions of the present invention described below.

Advansageous Effects

A modified butadiene-based polymer according to the present invention is modified using a modifier including a functional group exhibiting excellent affinity for an inorganic filler or a solvent used during a polymer modifying process together with a functional group capable of enhancing dispersability of the inorganic filler, and therefore, is capable of enhancing dispersability of the inorganic filler when used in a rubber composition, and enhancing viscoelasticity, a tensile property and processibility of the rubber composition in a balanced way from an interaction with the inorganic filler. Accordingly, the modified butadiene-based polymer may be used in various rubber compositions, and particularly, is capable of enhancing abrasion resistance as well as fuel efficiency properties when used in rubber compositions for tires.

MODE FOR CARRYING OUT THE INVENTION

Hereinafter, the present invention will be described in more detail in order to illuminate the present invention. Terms or words used in the present specification and the claims are not to be interpreted limitedly to common or dictionary definitions, and shall be interpreted as meanings and concepts corresponding to technological ideas of the present invention based on a principle in which the inventors may suitably define the concepts of terms in order to describe the invention in the best possible way.

A term 'combination thereof' used in the present specification means two or more functional groups directly bonding to form a single bond, or bonding with a divalent hydrocarbon group, or a divalent hydrocarbon group including one or more heteroatoms such as O, S, or N in the molecule, or two or more substituents being linked through condensation, unless particularly stated otherwise.

One embodiment of the present invention provides a modified butadiene-based polymer including a modifier-derived functional group of the following Chemical Formula 1 as a modified polymer of a lanthanide rare earth element-catalyzed butadiene-based polymer.

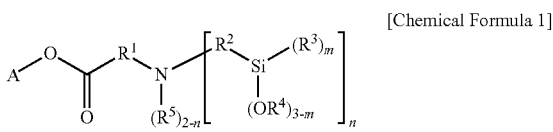

[Chemical Formula 1]

In Chemical Formula 1,

A is a hydrocarbon group having 1 to 20 carbon atoms, or a hydrocarbon group having 1 to 20 carbon atoms including one or more heteroatoms selected from the group consisting of N, S and O, $R^1$ and $R^2$ are each independently a divalent hydrocarbon group having 1 to 20 carbon atoms unsubstituted or subsituted with one or more substituents selected from the group consisting of a linear or branched alkyl group having 1 to 20 carbon atoms, a cycloalkyl group having 3 to 20 carbon atoms and an aryl group having 6 to 30 carbon atoms, $R^3$ to $R^5$ are each independently a monovalent hydrocarbon group having 1 to 20 carbon atoms, m is an integer of 0 to 3, and n is an integer of 1 or 2, but when A is a hydrocarbon group having 1 to 20 carbon atoms, n is an integer of 2.

Specifically, the modified butadiene-based polymer is prepared by reacting a butadiene-based polymer having an active site with the modifier, and the modifier modifies a polymer by providing, in a butadiene-based polymer, specifically, a butadiene-based polymer having an active organic metal site, a functional group to the butadiene-based polymer through a substitution or addition reaction with the active organic metal site.

In the present invention, an active site of a butadiene-based polymer may be an active end site (an active site of a molecular chain end), an active site in the main chain or an active site in the side chain of the butadiene-based polymer, and among these, may be an active end site of the butadiene-based polymer when obtaining an active site of the butadiene-based polymer from anionic coordination polymerization.

The modifier of Chemical Formula 1 used for preparing the modified butadiene-based polymer according to one embodiment of the present invention includes, in addition to a reactive functional group for the butadiene-based polymer, a functional group for enhancing inorganic filler dispersability, and at least one of an inorganic filler-friendly functional group and a solvent-friendly functional group in the molecule as a functional group capable of improving physical properties of the butadiene-based polymer.

Specifically, the modifier of Chemical Formula 1 is capable of modifying a butadiene-based polymer in a high modification rate by including an ester group having high reactivity for an active site of the butadiene-based polymer, and as a result, the substituted functional group in the modifier may be introduced to the butadiene-based polymer in a high yield. In addition, the modifier includes an amino group, specifically a tertiary amino group, as a functional group capable of enhancing inorganic filler dispersability by preventing aggregation between the inorganic fillers in a rubber composition. As one example, when using silica as an inorganic filler, aggregation readily occurs due to hydrogen bonding between hydroxyl groups present on the surface. In this regard, by including a tertiary amino group that inhibits hydrogen bonding between hydroxyl groups in the modifier, silica dispersability may be enhanced. In addition, the modifier includes, together with the above-mentioned amino group, at least one type of an inorganic filler-friendly functional group capable of enhancing abrasion resistance and processability of a rubber composition due to interaction with the inorganic filler, and a solvent-friendly functional group having excellent affinity for solvents used in a butadiene-based polymer modification reaction. The inorganic filler-friendly functional group is specifically an alkoxysilyl group, and is capable of enhancing abrasion resistance and processability of a butadiene-based polymer through a condensation reaction with a functional group on the inorganic filler surface, for example, a silanol group on a silica surface when the inorganic filler is silica, after being introduced to the butadiene-based polymer. Such an improving effect is enhanced as the number of the alkoxysilyl groups increases. In addition, the solvent-friendly functional group is specifically a hydrocarbon group such as an alkyl group or an aryl group, and increases solubility of a modifier for a solvent in a modification process for a butadiene-based polymer, and as a result, a modification rate of the butadiene-based polymer may be enhanced.

Specifically, in Chemical Formula 1, A is a hydrocarbon group having 1 to 20 carbon atoms, or a hydrocarbon group having 1 to 20 carbon atoms including one or more heteroatoms selected from the group consisting of N, S and O.

More specifically, when A is a hydrocarbon group having 1 to 20 carbon atoms, A may be selected from the group consisting of an alkyl group having 1 to 20 carbon atoms, a cycloalkyl group having 3 to 20 carbon atoms, an aryl group having 6 to 20 carbon atoms and an arylalkyl group having 7 to 20 carbon atoms, and even more specifically, A may be selected from the group consisting of an alkyl group having 1 to 10 carbon atoms, a cycloalkyl group having 3 to 12 carbon atoms, an aryl group having 6 to 12 carbon atoms and an arylalkyl group having 7 to 12 carbon atoms.

In addition, when A is a hydrocarbon group having 1 to 20 carbon atoms including a heteroatom, A may be those including heteroatoms instead of one or more carbon atoms in the hydrocarbon group; or those substituting one or more hydrogen atoms bonding to a carbon atom in the hydrocarbon group with heteroatoms, or heteroatom-including functional groups, and herein, the heteroatom may be selected from the group consisting of N, O and S, and any one, two or more of these may be included. More specifically, when A is a hydrocarbon group having 1 to 20 carbon atoms including a heteroatom, A may be a hydrocarbon group having 1 to 20 carbon atoms including one or more functional groups selected from the group consisting of an alkoxy group; a phenoxy group; a carboxyl group; an acid anhydride group; an amino group; an amide group; an epoxy group; a mercapto group; $-[R^{11}O]_xR^{12}$ (herein, $R^{11}$ is an alkylene group having 2 to 20 carbon atoms, $R^{12}$ is selected from the group consisting of a hydrogen atom, an alkyl group having 1 to 20 carbon atoms, a cycloalkyl group having 3 to 20 carbon atoms, an aryl group having 6 to 20 carbon atoms and an arylalkyl group having 7 to 20 carbon atoms, and x is an integer of 2 to 10); a hydroxyl group, an alkoxy group, a phenoxy group, a carboxyl group, an ester group, an acid anhydride group, an amino group, an amide group, an epoxy group and a mercapto group (for example, a hydroxyalkyl group, an alkoxyalkyl group, a phenoxyalkyl group, an aminoalkyl group, a thiolalkyl group, or the like). Even more specifically, when A is an alkyl group having 1 to 20 carbon atoms including a heteroatom, A may be selected from the group consisting of an alkoxy group having 1 to 20 carbon atoms, an alkoxyalkyl group having 2 to 20 carbon atoms, a phenoxyalkyl group having 7 to 20 carbon atoms, an aminoalkyl group having 1 to 20 carbon atoms and $-[R^{11}O]_xR^{12}$ (herein, $R^{11}$ is an alkylene group having 2 to 10 carbon atoms, $R^{12}$ is selected from the group consisting of a hydrogen atom, an alkyl group having 1 to 10 carbon atoms, a cycloalkyl group having 3 to 12 carbon atoms, an aryl group having 6 to 18 carbon atoms and an arylalkyl group having 7 to 18 carbon atoms, and x is an integer of 2 to 10).

In addition, in Chemical Formula 1, $R^1$ and $R^2$ are each independently a divalent hydrocarbon group having 1 to 20 carbon atoms, and specifically, may be an alkylene group having 1 to 10 carbon atoms such as a methylene group, an ethylene group or a propylene group; an arylene group having 6 to 20 carbon atoms such as a phenylene group; or an arylalkylene group having 7 to 20 carbon atoms as a combination group thereof. More specifically, $R^1$ and $R^2$ may be each independently an alkylene group having 1 to 5 carbon atoms, and even more specifically, $R^1$ may be an alkylene group having 2 to 3 carbon atoms, and $R^2$ may be an alkylene group having 1 to 3 carbon atoms. In addition, $R^1$ and $R^2$ may be each independently substituted with one or more substituents selected from the group consisting of a linear or branched alkyl group having 1 to 20 carbon atoms, a cycloalkyl group having 3 to 20 carbon atoms and an aryl group having 6 to 30 carbon atoms.

Furthermore, in Chemical Formula 1, $R^3$ to $R^5$ are each independently a monovalent hydrocarbon group having 1 to 20 carbon atoms, and specifically, may be selected from the group consisting of an alkyl group having 1 to 10 carbon atoms, a cycloalkyl group having 3 to 18 carbon atoms, an aryl group having 6 to 18 carbon atoms and a combination group thereof. More specifically, $R^3$ and $R^4$ are each independently an alkyl group having 1 to 5 carbon atoms, and $R^5$ may be an alkyl group having 1 to 5 carbon atoms or a cycloalkyl group having 3 to 8 carbon atoms. Even more specifically, $R^3$ to $R^5$ may be each independently an alkyl group having 1 to 5 carbon atoms.

In addition, in Chemical Formula 1, m is an integer of 0 to 3, and more specifically an integer of 0 to 2. In addition, n is an integer of 1 or 2, but when A is a hydrocarbon group having 1 to 20 carbon atoms, n is an integer of 2.

More specifically, in the modifier of Chemical Formula 1, A is any one selected from the group consisting of an alkyl group having 1 to 10 carbon atoms, a cycloalkyl group having 3 to 12 carbon atoms, an aryl group having 6 to 12 carbon atoms, an arylalkyl group having 7 to 12 carbon atoms, an alkoxyalkyl group having 2 to 10 carbon atoms, a phenoxyalkyl group having 7 to 12 carbon atoms, an aminoalkyl group having 1 to 10 carbon atoms and $-[R^{11}O]_xR^{12}$ (herein, $R^{11}$ is an alkylene group having 2 to 10 carbon atoms, $R^{12}$ selected from the group consisting of a hydrogen atom, an alkyl group having 1 to 10 carbon atoms, a cycloalkyl group having 3 to 12 carbon atoms, an aryl group having 6 to 18 carbon atoms and an arylalkyl group having 7 to 18 carbon atoms, and x is an integer of 2 to 10), $R^1$ and $R^2$ are each independently an alkylene group having 1 to 5 carbon atoms, $R^3$ and $R^4$ are each independently an alkyl group having 1 to 5 carbon atoms, $R^5$ is an alkyl group having 1 to 5 carbon atoms or a cycloalkyl group having 3 to 8 carbon atoms, m is an integer of 0 to 2 and n is an integer of 1 or 2, but when A is an alkyl group having 1 to 10 carbon atoms, a cycloalkyl group having 3 to 12 carbon atoms, an aryl group having 6 to 12 carbon atoms or an arylalkyl group having 7 to 12 carbon atoms, n is an integer of 2.

Even more specifically, the modifier may be 2-methoxyethyl 3-(bis(3-triethoxysilyl)propyl)amino)propanoate, 2-phenoxyethyl 3-(bis(3-(triethoxysilyl)propyl)amino)propanoate, 2-methoxyethyl 3-(bis(3-(diethoxy(methyl)silyl)propyl)amino)propanoate, 2-ethoxyethyl 2-ethoxyethyl 3-(bis(3-(diethoxy(methyl)silyl)propyl)amino)propanoate, ethyl 3-(bis(3-(diethoxy(methyl)silyl)propyl)amino)propanoate, 2-phenoxyethyl 3-(cyclohexyl((triethoxysilyl)methyl)amino)propanoate, 2-methoxyethyl 3-(cyclohexyl((triethoxysilyl)methyl)amino)propanoate, 2-dimethylaminoethyl 3-(cyclohexyl((triethoxysilyl)methyl)amino)propanoate, 2,5,8,11,14,17,20,23,26-nonaoxaoctacosan-28-yl 3-(bis(3-(triethoxysilyl)propyl)amino)propanoate, 2-(2-(2-(2-phenoxyethoxy)ethoxy)ethoxy)ethyl 3-(bis(3-(triethoxysilyl)propyl)amino)propanoate, 2-(dimethylamino) ethyl 3-(bis(3-(triethoxysilyl)propyl)amino)propanoate, 2-(2-(2-(2-phenoxyethoxy)ethoxy)ethoxy)ethyl 3-(cyclohexyl((triethoxysilyl)methyl)amino)propanoate, 2-methoxyethyl 3-(bis(3-(diethyoxy(methyl)silyl)propyl)amino)propanoate,ethyl 3-(bis(3-(diethoxy(methyl)silyl)propyl)amino)propanoate or the like, and any one or a mixture of two or more of these may be used.

Among these, the modifier of Chemical Formula 1 may be a compound in which A is any one selected from the group consisting of an alkyl group having 1 to 10 carbon atoms, an alkoxyalkyl group having 2 to 10 carbon atoms and a phenoxyalkyl group having 7 to 12 carbon atoms, $R^1$ and $R^2$ are each independently an alkylene group having 1 to 5 carbon atoms, $R^3$ and $R^4$ are each independently an alkyl group having 1 to 5 carbon atoms, m is is an integer of 0 or 1, and n is an integer of 2, and specific examples thereof may include 2-methoxyethyl 3-(bis(3-triethoxysilyl)propyl) amino)propanoate, 2-phenoxyethyl 3-(bis(3-(triethoxysilyl)propyl)amino)propanoate, 2-methoxyethyl 3-(bis(3-(diethoxy(methyl)silyl)propyl)amino)propanoate,2-ethoxyethyl 3-(bis(3-diethoxy(methyl)silyl)propyl)amino)propanoate, ethyl 3-(bis(3-(diethoxy(methyl)silyl)propyl)amino)propanoate, or the like.

As described above, the modifier has an optimized structure capable of maximizing affinity for an inorganic filler and a solvent, and as a result, a modified butadiene-based polymer having excellent viscoelasticity, tensile property and processibility may be efficiently prepared.

More specifically, the modifier may have solubility of 10 g or more for a nonpolar solvent, more specifically 100 g of hexane, at 25° C. and 1 atmosphere. In the present invention, solubility of the modifier means being clearly dissolved without turbidity when observed visually. By having such high solubility, an excellent modification rate for a butadiene-based polymer may be obtained.

Meanwhile, the butadiene-based polymer may be a butadiene homopolymer such as polybutadiene, or a butadiene copolymer such as a butadiene-isoprene copolymer.

Accordingly, the butadiene-based polymer may specifically include a 1,3-butadiene monomer unit in 80% by weight to 100% by weight, and selectively include other butadiene-based monomer units copolymerizable with 1,3-butadiene in 20% by weight or less. When the 1,3-butadiene monomer unit content in the butadiene-based polymer is less than 80% by weight, 1,4-cis bone content in the polymer may decrease. Herein, as the 1,3-butadiene monomer, 1,3-butadiene or derivatives thereof such as 1,3-butadiene, 2,3-dimethyl-1,3-butadiene or 2-ethyl-1,3-butadiene may be included, and as the other butadiene-based monomers copolymerizable with the 1,3-butadiene may specifically include 2-methyl-1,3-pentadiene, 1,3-pentadiene, 3-methyl-1,3-pentadiene, 4-methyl-1,3-pentadiene, 1,3-hexadiene, 2,4-hexadiene or the like, and any one, two or more compounds of these may be used.

More specifically, the butadiene-based polymer may be a butadiene-based polymer including an active organic metal site derived from a catalyst including a lanthanide rare earth element-containing compound, and even more specifically, neodymium-catalyzed 1,4-cis polybutadiene including a 1,3-butadiene monomer unit.

In addition, the modified butadiene-based polymer according to one embodiment of the present invention may have properties such as optimized molecular weight distribution, Mooney viscosity and the like so that viscoelasticity, a tensile property and processibility of a rubber composition are improved in a balanced way through controlling a catalyst composition, a polymerization condition and the like in the preparation.

Specifically, the modified butadiene-based polymer may have narrow molecular weight distribution (Mw/Mn) of 2.5 to 3.5. When the molecular weight distribution of the modified butadiene-based polymer is greater than 3.5 or less than 2.5, there is concern that a tensile property and viscoelasticity may decline when the modified butadiene-based polymer is used in a rubber composition. When considering the significance of tensile property and viscoelasticity improving effects of the polymer obtained from controlling molecular weight distribution, the modified butadiene-based polymer may specifically have molecular weight distribution of 3.0 to 3.2.

In the present invention, molecular weight distribution of the modified butadiene-based polymer may be calculated from a ratio (Mw/Mn) of a weight average molecular weight (Mw) to a number average molecular weight (Mn). Herein, the number average molecular weight (Mn) is a common average of individual molecular weights of polymers calculated by measuring molecular weights of n polymer molecules, and dividing the sum of these molecular weights by n, and the weight average molecular weight (Mw) represents molecular weight distribution of a polymer composition. All molecular weight averages may be represented by gram per mol (g/mol).

Furthermore, in the present invention, the weight average molecular weight and the number average molecular weight are each a polystyrene converted molecular weight analyzed with gel permeation chromatography (GPC).

In addition, the modified butadiene-based polymer according to one embodiment of the present invention may have a weight average molecular weight (Mw) of $5 \times 10^5$ g/mol to $1.2 \times 10^6$ g/mol and specifically $9 \times 10^5$ g/mol to $1.0 \times 10^6$ g/mol while satisfying the above-mentioned molecular weight distribution condition. In addition, the modified butadiene-based polymer according to one embodiment of the present invention may have a number average molecular weight (Mn) of $1.5 \times 10^5$ g/mol to $3.5 \times 10^5$ g/mol and specifically $3.0 \times 10^5$ g/mol to $3.2 \times 10^5$ g/mol. When the modified butadiene-based polymer has a weight average molecular weight (Mw) of less than $5 \times 10^5$ g/mol or a number average molecular weight (Mn) of less than $1.5 \times 10^5$ g/mol, a tensile property may decline when used in a rubber composition. When the weight average molecular weight (Mw) is greater than $1.2 \times 10^6$ g/mol or the number average molecular weight (Mn) is greater than $3.5 \times 10^5$ g/mol, processibility of the modified butadiene-based polymer declines causing degeneration in the workability of a rubber composition, and mixing and kneading become difficult, and as a result, physical properties of the rubber composition may be difficult to be sufficiently enhanced.

More specifically, when satisfying both the weight average molecular weight (Mw) condition and the number average molecular weight condition together with the above-mentioned molecular weight distribution, the modified butadiene-based polymer according to one embodiment of the present invention is capable of improving a tensile property, viscoelasticity and processibility for a rubber composition in a balanced way without inclining to any one of these when used in the rubber composition.

In addition, the modified butadiene-based polymer according to one embodiment of the present invention may have Mooney viscosity (MV) of 40 to 70 and specifically 60 to 65 at 100° C. When the Mooney viscosity is obtained in the above-mentioned range, more excellent processibility may be obtained.

In the present invention, Mooney viscosity may be measured using a Mooney viscometer, for example, a Large Rotor of MV2000E manufactured by Monsanto under a condition of 100° C. and Rotor Speed 2±0.02 rpm. Herein, the sample is left unattended for 30 minutes or longer at room temperature (23±3° C.), 27±3 g thereof is collected and inside a die cavity is filled with the sample, and Mooney viscosity may be measured while operating a Platen.

More specifically, when satisfying the Mooney viscosity condition together with the molecular weight distribution, the weight average molecular weight (Mw) and the number average molecular weight (Mn) described above, the modified butadiene-based polymer according to one embodiment of the present invention is capable of improving all of a tensile property, viscoelasticity and processibility for a rubber composition in a balanced way when used in the rubber composition. Specifically, the modified butadiene-based polymer may have molecular weight distribution of 2.5 to 3.5, a weight average molecular weight (Mw) of $5 \times 10^5$ g/mol to $1.2 \times 10^6$ g/mol, a number average molecular weight (Mn) of $1.5 \times 10^5$ g/mol to $3.5 \times 10^5$ g/mol, and Mooney viscosity of 40 to 70 at 100° C. Even more specifically, the modified butadiene-based polymer may have molecular weight distribution of 3.0 to 3.2, a weight average molecular weight (Mw) of $9 \times 10^5$ g/mol to $1.0 \times 10^6$ g/mol, a number average molecular weight (Mn) of $3.0 \times 10^5$ g/mol to $3.2 \times 10^5$ g/mol, and Mooney viscosity of 60 to 65 at 100° C.

A modified butadiene-based polymer according to one embodiment of the present invention having the structure and and the physical properties described above may be prepared using a preparation method including a modification step of reacting a butadiene-based polymer having a lanthanide rare earth element-catalyzed active organic metal site with the modifier of Chemical Formula 1.

Specifically, in order to react the the butadiene-based polymer active site and the modifier in the preparation of the modified butadiene-based polymer, the used butadiene-based polymer preferably has a living property or a pseudo living property. As a polymerization reaction of such a polymer having a living property, anionic coordination polymerization may be used.

Specifically, the butadiene-based polymer capable of being used in the modified butadiene-based polymer preparation may be prepared by polymerizing a butadiene monomer in an organic solvent using a catalyst for polymerization including a lanthanide rare earth element-containing compound.

In addition, the catalyst for polymerization specifically includes a lanthanide rare earth element-containing compound, an alkylating agent and a halogen compound.

In the catalyst for polymerization, the lanthanide rare earth element-containing compound may be a compound including any one, two or more elements among rare earth elements of atomic numbers 57 to 71 in the periodic table such as neodymium, praseodymium, cerium, lanthanum or gadolinium, and more specifically, a compound including neodymium.

In addition, the lanthanide rare earth element-containing compound may be a salt soluble in a hydrocarbon solvent such as carboxylates, alkoxides, β-diketone complexes, phosphates or phosphites of lanthanide rare earth elements, and even more specifically, the neodymium-containing carboxylate. The hydrocarbon solvent may include saturated aliphatic hydrocarbon having 4 to 10 carbon atoms such as butane, pentane, hexane and heptane; saturated alicyclic hydrocarbon having 5 to 20 carbon atoms such as cyclopentane and cyclohexane; monoolefins such as 1-butene and 2-butene; aromatic hydrocarbon such as benzene, toluene and xylene; or halogenated hydrocarbon such as methylene chloride, chloroform, trichloroethylene, perchloroethylene, 1,2-dichloroethane, chlorobenzene, bromobenzene or chlorotoluene.

Even more specifically, the lanthanide rare earth element-containing compound may be a neodymium compound of the following Chemical Formula 4:

[Chemical Formula 4]

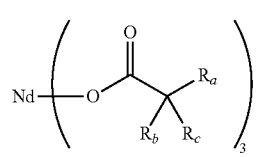

in Chemical Formula 4, $R_a$ to $R_c$ are each independently a hydrogen atom, or a linear or branched alkyl group having 1 to 12 carbon atoms.

Specifically, the neodymium compound may be any one or a mixture of two or more selected from the group consisting of Nd(neodecanoate)$_3$, Nd(2-ethylhexanoate)$_3$, Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isobutyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$ and Nd(2-ethyl-2-hexyl nonanoate)$_3$.

In addition, when considering excellent solubility for polymerization solvents, a conversion rate to catalyst active species and superiority of catalytic activity improving effects resulted therefrom without concern for oligomerization, the lanthanide rare earth element-containing compound may more specifically be a neodymium compound in which, in Chemical Formula 4, $R_a$ is a linear or branched alkyl group having 4 to 12 carbon atoms, and $R_b$ and $R_c$ are each independently a hydrogen atom or a linear or branched alkyl group having 2 to 8 carbon atoms, but $R_b$ and $R_c$ are not both hydrogen atoms at the same time.

Even more specifically, in Chemical Formula 4, $R_a$ is a linear or branched alkyl group having 6 to 8 carbon atoms, and $R_b$ and $R_c$ may be each independently a hydrogen atom or a linear or branched alkyl group having 2 to 6 carbon atoms, and herein, $R_b$ and $R_c$ are not both hydrogen atoms at the same time. Specific examples thereof may include Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isobutyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$, Nd(2-ethyl-2-hexyl nonanoate)$_3$ or the like, and among these, the neodymium compound may be any one or a mixture of two or more selected from the group consisting of Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, and Nd(2,2-dioctyl decanoate)$_3$.

Even more specifically, in Chemical Formula 4, $R_a$ is a linear or branched alkyl group having 6 to 8 carbon atoms, and $R_b$ and $R_c$ may be each independently a linear or branched alkyl group having 2 to 6 carbon atoms.

Thus, by the neodymium compound of Chemical Formula 4 including a carboxylate ligand including an alkyl group with various lengths of 2 or more carbon atoms as a substituent at an α position, coagulation between the compounds may be blocked by inducing stereoscopic changes around the neodymium central metal, and as a result, oligomerization may be suppressed. In addition, such a neodymium compound has high solubility for polymerization solvents, and has a high rate of conversion to an active catalyst species since the ratio of neodymium located in the central part having difficulties in being converted to an active catalyst species decreases.

The compound of Chemical Formula 4 may have a weight average molecular weight (Mw) of 600 g/mol to 2000 g/mol. When having such a weight average molecular weight range, excellent catalytic activity may be more stably obtained.

In addition, solubility of the lanthanide rare earth element-containing compound may be approximately 4 g or more per 6 g of a nonpolar solvent at room temperature (25° C.). In the present invention, solubility of the neodymium compound means a level of being clearly dissolved without turbidity. By having such high solubility, excellent catalytic activies may be obtained.

The lanthanide rare earth element-containing compound may be used in the content of 0.1 mmol to 0.5 mmol and more specifically 0.1 mmol to 0.2 mmol per 100 g of the butadiene-based monomer. When the amount of the used lanthanide rare earth element-containing compound is less than 0.1 mmol, catalytic activities for polymerization is low, and when greater than 0.5 mmol, catalyst concentration becomes too high, and a deliming process is required.

The lanthanide rare earth element-containing compound may be used in the form of a reactant with a Lewis base. This reactant enhances solubility of the lanthanide rare earth element-containing compound for a solvent by the Lewis base, and long term storage is also possible. In order to readily solubilize the lanthanide rare earth element-containing compound in a solvent, and to stably store the compound for a long period of ttime, the Lewis base may be used in a ratio of 30 mols or less and preferably in 1 mol to 10 mols per 1 mol of the rare earth element. In addition, the Lewis base may include acetylacetone, tetrahydrofuran, pyridine, N,N-dimethylformamide, thiophene, diphenyl ether, triethylamine, organic phosphorous compounds or primary or secondary alcohols, and the like.

In addition, in the catalyst for polymerization, the alkylating agent is an organic metal compound capable of transferring a hydrocarbyl group to other metals, and performs a role of a cocatalyst. As the alkylating agent, those commonly used as an alkylating agent in diene-based polymer preparation may be used without particular limit. Specifically, the alkylating agent may be an organic metal compound soluble in nonpolar solvents and containing metal-carbon bonds, such as an organic aluminum compound, an organic magnesium compound or an organic lithium compound.

Specific examples of the organic aluminum compound may include alkylaluminum such as trimethylaluminum, triethylaluminum, tri-n-propylaluminum, triisobutylaluminum, tri-n-butylaluminum, triisobutylaluminum, tri-t-butylaluminum, tripentylaluminum, trihexylaluminum, tricyclohexylaluminum or trioctylaluminum; dihydrocarbylaluminum hydride such as diethylaluminum hydride, di-n-propylaluminum hydride, diisobutylaluminum hydride, di-n-butylaluminum hydride, diisobutylaluminum hydride (DIBAH), di-n-octylaluminum hydride, diphenylaluminum hydride, di-p-tolylaluminum hydride, dibenzylaluminum hydride, phenylethylaluminum hydride, phenyl-n-propylaluminum hydride, phenylisobutylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisobutylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisobutylaluminum hydride, benzyl-n-butylaluminum hydride, benzylisobutylaluminum hydride or benzyl-n-octylaluminum hydride; hydrocarbylaluminum dihydride such as ethylaluminum dihydride, n-propylaluminum dihydride, isobutylaluminum dihydride, n-butylaluminum dihydride, isobutylaluminum dihydride or n-octylaluminum dihydride, and the like. In addition, specific examples of the organic magnesium compound may include alkylmagnesium compounds such as diethylmagnesium, di-n-propylmagnesium, diisobutylmagnesium, dibutylmagnesium, dihexylmagnesium, diphenylmagnesium or dibenzylmagnesium, and the like, and specific examples of the organic lithium compound may include alkyllithium compounds such as n-butyllithium, and the like.

As the alkylating agent, any one or a mixture of two or more of the organic aluminum compound, the organic magnesium compound and the organic lithium compound may be used, and more specifically, DIBAH capable of performing a role of a molecular weight modifier may be used.

In addition, the alkylating agent may be used in a molar ratio of 1 to 100 and more specifically 3 to 20 with respect to 1 mol of the lanthanide rare earth element-containing compound.

In the catalyst for polymerization, types of the halogen compound are not particularly limited, and those commonly used as halogenides in diene-based polymer preparation may be used without limit. Specifically, the halogen compound may be an aluminum halogen compound or an inorganic halogen compound substituting the aluminum in the aluminum halogen compound with boron, silicon, tin or titanium, or an organic halogen compound such as a t-alkyl halogen compound (alkyl having 4 to 20 carbon atoms).

More specifically, examples of the inorganic halogen compound may include dimethylaluminum chloride, diethylaluminumchloride (DEAC), dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, methylmagnesium iodide, ethylmagnesium chloride, ethylmagnesium bromide, butylmagnesium chloride, butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, dibutyltin dichloride, dibutyltin dibromide, tributyltin chloride, tributyltin bromide and the like.

In addition, examples of the organic halogen compound may include t-butyl chloride, t-butyl bromide, allyl chloride, allyl bromide, benzyl chloride, benzyl bromide, chloro-di-phenylmethane, bromo-di-phenylmethane, triphenylmethyl chloride, triphenylmethylbromide, benzyliden chloride, benzyliden bromide, methyltrichlorosilane, phenyltrichlorosilane, dimethyldichlorosilane, diphenyldichlorosilane, trimethylchlorosilane, benzoyl chloride, benzoyl bromide, propionyl chloride, propionyl bromide, methyl chloroformate, methyl bromoformate and the like.

As the halogen compound, any one or a mixture of two or more of the inorganic halogen compound and the organic halogen compounds may be used, and the halogen compound may be used in 1 mol to 5 mols and more specifically in 2 mols to 3 mols with respect to 1 mol of the lanthanide rare earth element-containing compound.

In addition, the catalyst for polymerization may further include a diene-based monomer.

By mixing some of the diene-based monomer used in the polymerization reaction with a catalyst for polymerization in advance, and using the result in the form of a preforming catalyst, catalytic activities may be enhanced, and the prepared diene-based polymer may be stabilized as well.

In the present invention, the "preforming" may mean pre-polymerization in a catalyst system carried out with a butadiene addition, since monomers such as butadiene are added in a small amount in order to reduce the possibility of various active catalyst species production when the catalyst system including a lanthanide rare earth element-containing compound, an alkylating agent and a halogen compound includes DIBAH and the like. In addition, "premix" may mean a state in which each compound is uniformly mixed in a catalyst system without being polymerized.

Specific examples of the diene-based monomer may include 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene or the like, and any one or a mixture of two or more of these may be used. The amount of the diene-based monomer capable of being used for preparing the catalyst for polymerization may be a partial amount in the total amount range of the diene-based monomer used in the polymerization reaction, and specifically, the amount may be in a molar ratio of 1 to 100, more specifically 10 to 50 and even more specifically 20 to 40 with respect to 1 mol of the lanthanide rare earth element-containing compound.

Such a catalyst for polymerization may be prepared by introducing the lanthanide rare earth element-containing compound, the alkylating agent, the halogen compound, and selectively the diene-based monomer in an organic solvent in consecutive order, and mixing the result. Herein, the organic solvent may be a nonpolar solvent having no reactivity for the above-mentioned catalyst constituents. Specifically, the organic solvent may include aliphatic hydrocarbon-based solvents such as pentane, hexane, isopentane, heptane, octane and isooctane; cycloaliphatic hydrocarbon-based solvents such as cyclopentane, methylcyclopentane, cyclohexane, methylcyclohexane and ethylcyclohexane; or aromatic hydrocarbon-based solvents such as benzene, toluene, ethylbenzene and xylene, and any one or a mixture of two or more types may be used. More specifically, the organic solvent may be aliphatic hydrocarbon-based solvents such as hexane.

In addition, a polymerization reaction of a butadiene-based polymer using the catalyst composition may be carried out using radical polymerization, and specifically using bulk polymerization, solution polymerization, suspension polymerization or emulsion polymerization, and more specifically using solution polymerization. Furthermore, the polymerization reaction may be carried out using any method of batch-type and continuous methods.

More specifically, the polymerization reaction for preparing a butadiene-based polymer may be carried out by introducing a butadiene-based monomer to the catalyst for polymerization and reacting the result in an organic solvent.

The butadiene monomer used for a butadiene-based polymer may include 1,3-butadiene or derivatives thereof, and more specifically, may include 1,3-butadiene, 2,3-dimethyl-1,3-butadiene, 2-ethyl-1,3-butadiene or the like, and any one or a mixture of two or more of these may be used.

In addition, with the monomer, other monomers copolymerizable with the monomer and a conjugated diene-based monomer may be selectively used. Herein, the other monomer including a conjugated diene-based monomer additionally used may be used in proper content considering physical properties of a finally prepared conjugated diene-based polymer. Specifically, the conjugated diene-based monomer capable of being additionally used may include 2-methyl-1,3-pentadiene, 1,3-pentadiene, 3-methyl-1,3-pentadiene, 4-methyl-1,3-pentadiene, 1,3-hexadiene, 2,4-hexadiene or the like, and any one or a mixture of two or more of these may be used.

The polymerization reaction for preparing a butadiene-based polymer may be carried out in an organic solvent.

The organic solvent may be additionally added to the amount of the organic solvent capable of being used for preparing the catalyst for polymerization, and herein, the organic solvent may be the same as the organic solvent described above. In addition, a concentration of the monomer is not particularly limited when using the organic solvent, and the concentration may be from 3% by weight to 80% by weight and more specifically from 10% by weight to 30% by weight.

In addition, during the polymerization reaction for preparing a butadiene-based polymer, additives such as a reaction terminating agent such as polyoxyethylene glycol phosphate for completing the polymerization reaction; or an antioxidant such as 2,6-di-t-butylparacresol may be further used. In addition to these, additivies commonly used for facilitating solution polymerization, specifically, additives such as a chelating agent, a dispersion agent, a pH controlling agent, a deoxidizer or an oxygen scavenger may be further used selectively.

The polymerization reaction for preparing a butadiene-based polymer may be carried out for 15 minutes to 3 hours and more specifically for 30 minutes to 2 hours at a temperature of 20° C. to 200° C. and more specifically 20° C. to 100° C. When the temperature during the polymerization reaction is higher than 200° C., the polymerization reaction is difficult to be sufficiently controlled, and there is concern of a cis-1,4 bond content decrease in the produced diene-based polymer. When the temperature is lower than 20° C., there is concern of decreases in the polymerization reaction rate and efficiency.

In addition, the polymerization reaction for preparing a butadiene-based polymer preferably prevents mixing of compunds having devitalizing function such as oxygen, water and carbon dioxide into the polymerization reaction system in order to prevent devitalization of the rare earth element compound-based catalyst and the polymer.

The polymerization reaction for a butadiene-based polymer may terminate the polymerization reaction by adding an isopronanol solution of 2,6-di-t-butyl-p-cresol (BHT) to the polymerization reaction system. After that, desolventizing treatment such as steam stripping lowering a solvent partial pressure through vapor supply, or a vacuum drying process may be further carried out selectively.

As a result of such a polymerization reaction, a butadiene-based polymer including an active organic metal site derived from a catalyst including the lanthanide rare earth element-containing compound, more specifically, a neodymium-catalyzed butadiene-based polymer including a 1,3-butadiene monomer unit is produced. The prepared butadiene-based polymer may have a pseudo living property.

Meanwhile, modification in the modified butadiene-based polymer preparation according to one embodiment of the present invention may be carried out by adding the modifier to the butadiene-based polymer prepared through such a preparation process in greater than a stoichiometric amount with respect to the active organic metal site of the butadiene-based polymer, and thereby reacting the modifier with active organic metal site binding to the polymer. Herein, the modifier may be used in a molar ratio of 0.5 to 20 and more specifically 0.1 to 10 with respect to 1 mol of the lanthanide rare earth element-containing compound used in the preparation of the butadiene-based polymer having an active site.

The modification reaction may be carried out using a solution reaction or a solid state reaction, and specifically, may be carried out using a solution reaction.

In addition, the modification reaction may be carried out using a batch-type reactor, or may be continuously carried out using devices such as a multi-stage continuous reactor or an inline mixer.

Furthermore, the modification reaction may be commonly carried out under the same temperature and pressure conditions as the polymerization reaction, and specifically, may be carried out at a temperature of 20° C. to 100° C. When the temperature decreases, viscosity of the polymer tends to increase, and when the temperature increases, polymerization active ends are readily deactivated.

The method for preparing a modified butadiene-based polymer according to one embodiment of the present invention may further include precipitation and separation processes for the prepared modified butadiene-based polymer. Filtering, separating and drying processes for the precipitated modified butadiene-based polymer may be carried out using common methods.

As described above, using the method for preparing a modified butadiene-based polymer according to one embodiment of the present invention, a modified butadiene-based polymer having excellent physical properties including narrow molecular weight distribution, more specifically, a neodymium-catalyzed butadiene-based polymer, may be prepared.

Another embodiment of the present invention provides a rubber composition including the modified butadiene-based polymer.

Specifically, the rubber composition may include the modified butadiene-based polymer in 10% by weight or greater and more specifically in 10% by weight to 100% by weight. When the butadiene-based polymer content is less than 10% by weight, effects of improving abrasion resistance, crack resistance and ozone resistance of the rubber composition may be insignificant.

In addition, the rubber composition may further include a rubber component together with the modified butadiene-based polymer in the content of 90% by weight or less with respect to the total weight of the rubber composition. More specifically, the rubber component may be further included in 1 parts by weight to 900 parts by weight with respect to 100 parts by weight of the modified butadiene-based polymer.

The rubber component may be natural rubber or synthetic rubber, and specific examples of the rubber component may include natural rubber (NR) including cis-1,4-polyisoprene; modified natural rubber such as epoxidized natural rubber (ENR), deproteinised natural rubber (DPNR) and hydrogenated natural rubber modifying or purifying the general natural rubber; synthetic rubber such as a styrene-butadiene copolymer (SBR), polybutadiene (BR), polyisoprene (IR), butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and halogenated butyl rubber, and any one or a mixture of two or more of these may be used.

In addition, the rubber composition may further include a filler in 10 parts by weight or greater and more specifically in 10 parts by weight to 120 parts by weight with respect to 100 parts by weight of the modified butadiene-based polymer.

The filler may be silica, and specifically, wet silica (hydrous silicate), dry silica (anhydrous silicate), calcium silicate, aluminum silicate, colloidal silica or the like. More specifically, the filler may be wet silica having most significant effects both in a fracture property improving effect and a wet grip property.

Meanwhile, in order to improve reinforcement and low heating properties when using silica as the filler, a silane coupling agent may also be used.

Specific examples of the silane coupling agent may include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 3-trimethoxysilylpropylbenzothiazolyl tetrasulfide, 3-triethoxysilylpropylbenzolyl tetrasulfide, 3-triethoxysilylpropyl methacrylate monosulfide, 3-trimethoxysilylpropyl methacrylate monosulfide, bis(3-diethoxymethylsilylpropyl)tetrasulfide, 3-mercaptopropyldimethoxymethylsilane, dimethoxymethylsilylpropyl-N,N-dimethylthiocarbamoyl tetrasulfide, dimethoxymethylsilylpropylbenzothiazolyl tetrasulfide and the like, and any one or a mixture of two or more of these may be used. More specifically, when considering an effect of improvement in the reinforcement, the silane coupling agent may be bis(3-triethoxysilylpropyl)polysulfide or 3-trimethoxysilylpropylbenzothiazyl tetrasulfide.

In addition, in the rubber composition according to one embodiment of the present invention, the mixed amount of the silane coupling agent mixed may be reduced compared to a normally used amount since a modified polymer having a functional group with high affinity for silica in an active site is used as the rubber component. Specifically, the silane coupling agent may be used in 1 part by weight to 20 parts by weight with respect to 100 parts by weight of the silica. When used in the above-mentioned range, gelation of the rubber component may be prevented while sufficiently exhibiting effects as a coupling agent. More specifically, the silane coupling agent may be used in 5 parts by weight to 15 parts by weight with respect to 100 parts by weight of the silica.

In addition, the rubber composition according to one embodiment of the present invention may be sulfur vulcanizable, and accordingly, may further include a vulcanizing agent.

The vulcanizing agent may be specifically sulfur powder, and may be included in 0.1 parts by weight to 10 parts by weight with respect to 100 parts by weight of the rubber component. When included in the above-mentioned content range, elastic modulus and strength required for vulcanized rubber composition may be secured, and high fuel efficiency may be obtained as well.

In addition, the rubber composition according to one embodiment of the present invention may further include, in addition to the above-mentioned components, various additives commonly used in a rubber industry, specifically, a vulcanization accelerator, process oil, a plasticizer, an antiaging agent, an antiscorching agent, zinc white, stearic acid, a thermocuring resin, a thermoplastic resin or the like.

The vulcanization accelerator is not particularly limited, and specific examples thereof may include thiazole-based compounds such as M (2-mercaptobenzothiazole), DM (dibenzothiazyl disulfide) and CZ (N-cyclohexyl-2-benzothiazyl sulfenamide), or guanidine-based compounds such as DPG (diphenyl guanidine). The vulcanization accelerator may be included in 0.1 parts by weight to 5 parts by weight with respect to 100 parts by weight of the rubber component.

The process oil functions as a softner in the rubber composition, and may specifically include paraffin-based, naphthene-based or aromatic based compounds, and more specifically, aromatic-based process oil may be used when considering tensile strength and abrasion resistance, and naphthene-based or paraffin-based process oil may be used when considering hysteresis low and a low temperature property. The process oil may be included in 100 parts by weight or less with respect to 100 parts by weight of the rubber component, and when included in the above-mentioned content, decline in the tensile strength and the low heating property (fuel efficiency property) may be prevented.

Specific examples of the antiaging agent may include N-isobutyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, high temperature condensates of diphenylamine and acetone, or the like. The antiaging agent may be used in 0.1 parts by weight to 6 parts by weight with respect to 100 parts by weight of the rubber component.

The rubber composition according to one embodiment of the present invention may be obtained by mixing the above-mentioned components in the above-mentiond mixting ratio using a mixer such as a banbury mixer, a roll and an internal mixer, and a rubber composition having a low heating property and excellent abrasion resistance may be obtained through a vulcanization process after a molding process.

As a result, the rubber composition may be useful for preparing each member of tires such as tire treads, under treads, side walls, carcass coating rubber, belt coating rubber, bead fillers, chafers or bead coating rubber, or various industrial rubber products such as vibration proof rubber, belt conveyers or hoses.

Another embodiment of the present invention provides a modifier useful for preparing the modified butadiene-based polymer. Herein, the modifier is the same as the modifier described above.

In addition, the modifier of Chemical Formula 1 according to one embodiment of the present invention may be prepared from a reaction of a compound of the following Chemical Formula 2 and a compound of the following Chemical Formula 3.

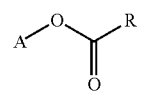

[Chemical Formula 2]

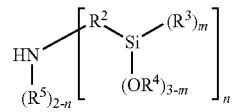

[Chemical Formula 3]

In Chemical Formulae 2 and 3, A, $R^2$ to $R^5$, m and n are the same as those described above, and R may be an alkenyl group having 2 to 20 carbon atoms unsubstituted or subsituted with one or more substituents selected from the group consisting of a linear or branched alkyl group having 1 to 20 carbon atoms, a cycloalkyl group having 3 to 20 carbon atoms and an aryl group having 6 to 30 carbon atoms.

More specifically, in Chemical Formula 2, R may be an alkenyl group having 2 to 10 carbon atoms, and more specifically, may be an alkenyl group having 2 to 5 carbon atoms such as an ethylene group.

Even more specifically, the compound of Chemical Formula 2 may be ethylene glycol methyl ether acrylate, 2-phenoxyethyl acrylate, ethyl acrylate and the like. In addition, the compound of Chemical Formula 3 may be bis[3-(triethoxysilyl)propyl]amine, bis(methyldiethoxysilyl-propyl)amine or the like.

The compounds of Chemical Formulae 2 and 3 may be used in stoichiometric amounts, and specifically, the compound of Chemical Formula 3 may be used in a molar ratio of 0.01 to 0.2, more specifically 0.05 to 0.1 and even more specifically 0.05 to 0.08 with respect to 1 mol of the compound of Chemical Formula 2.

In addition, the reaction of the compound of Chemical Formula 2 and the compound of Chemical Formula 3 may be carried out in an aqueous solvent. Specific examples of the aqueous solvent may include alcohols (for example, lower alcohols having 1 to 5 carbon atoms such as ethanol), and any one or a mixture of two or more of these may be used.

The reaction of the compound of Chemical Formula 2 and the compound of Chemical Formula 3 may be carried out under inert gas atmosphere. Specific examples of the inert gas may include nitrogen, argon and the like.

In addition, the reaction of the compound of Chemical Formula 2 and the compound of Chemical Formula 3 may be carried out in a temperature range of 20° C. to 60° C. When the temperature during the reaction is 20° C. or less, the reaction rate becomes too low and reaction efficiency may decrease, and when the temperature during the reaction is greater than 60° C., the reaction rate becomes too high making the reaction difficult to control, and side reactions may occur as well.

Using a preparation method as described above, a modifier including both a filler-friendly functional group and a solvent-friendly functional group in the single molecule may be readily prepared.

Hereinfter, examples of the present invention will be described in detail for those skilled in the art to readily carry out the invention. However, the present invention may be implemented in various different forms, and is not limited to the examples described herein.

PREPARATION EXAMPLE 1

Preparation of 2-methoxyethyl 3-(bis(3-(triethoxysilyl)propyl)amino)propanoate

In a 50 ml round bottom flask, 10 ml of ethanol was added to dissolve 0.823 mmol of bis(3-triethoxysilylpropyl)amine (Gelest, Inc.), then 11.364 mmol of ethyleneglycol methyl ether acrylate was added thereto, and the result was stirried for 8 hours at room temperature (25° C.) under nitrogen atmosphere to be reacted. After the reaction was complete, the solvent in the reaction material of the result was removed under vacuum, and the result was vacuum distilled at 120° C. to obtain 11.538 mmol of 2-methoxyethyl 3-(bis(3-(triethoxysilyl)propyl)amino)propanoate (i) of the following structure (yield 96.9%). The obtained compound was purified, and 1H and 13C Nuclear Magnetic Resonance spectroscopic spectra were observed.

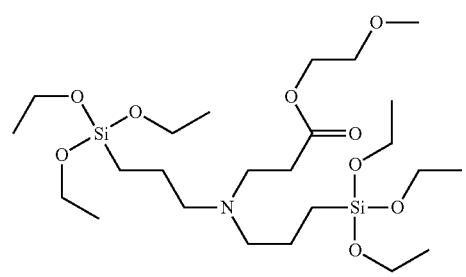

(i)

$^1$H-NMR (500 MHz, CDCl$_3$) δ 4.21-4.19 (t, 2H), δ 3.81-3.77 (m, 12H), δ 3.57-3.56 (t, 2H), δ 3.36 (s, 3H), δ 2.79-2.76 (t, 2H), δ 2.47-2.44 (t, 2H), δ 2.40-2.37 (t, 4H), δ 1.54-1.47 (m, 4H), δ 1.22-1.19 (t, 18H), δ 0.57-0.54 (t, 4H); $^{13}$C NMR (125 mHz, CDCl$_3$) δ172.8, 77.2, 77.0, 76.7, 63.3, 58.9, 56.8, 49.3, 32.4, 18.2, 7.9

PREPARATION EXAMPLE 2

Preparation of 2-phenoxyethyl 3-(cyclohexyl((triethoxysilyl)methyl)amino)propanoate In a 50 ml round bottom flask, 5 ml of ethanol was added to dissolve 5.744 mmol of (N-cyclohexylaminomethyl)triethoxysilane (Gelest, Inc.), then 5.744 mmol of 2-phenoxyethyl acrylate (TCI Co., Ltd.) was added thereto, and the result was stirried for 8 hours at room temperature under nitrogen atmosphere. After the reaction was complete, the solvent was removed under vacuum, and the result was vacuum distilled at 120° C. to obtain 4.990 mmol of 2-phenoxyethyl 3-(cyclohexyl((triethoxysilyl)methyl) amino)propanoate (ii) (yield 91.4%). 1H Nuclear Magnetic Resonance spectroscopic data of the purified 2-phenoxyethyl 3-(cyclohexyl((triethoxysilyl)methyl)amino)propanoate are as follows.

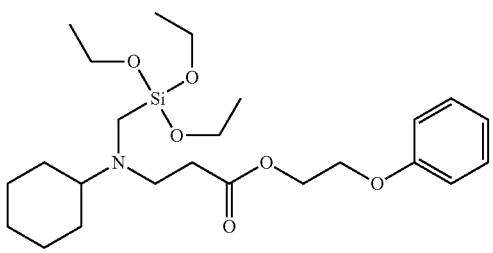

(ii)

$^1$H-NMR (500 MHz, CDCl$_3$) δ 7.49-7.23 (m, 2H), δ 6.97-6.86 (m, 3H), δ4.40-4.36 (m, 2H), δ 4.16-4.03 (m, 4H), δ 3.87-3.81 (m, 3H), δ 2.78-2.75 (m, 2H), δ 2.50-2.41 (m, 4H), δ 2.17-2.11 (m, 3H), δ 1.72-1.56 (m, 7H), δ1.26-1.16 (m, 12H)

PREPARATION EXAMPLE 3

Preparation of 2-methoxyethyl 3-(cyclohexyl((triethoxysilyl)methyl)amino)propanoate In a 50 ml round bottom flask, 5 ml of ethanol was added to dissolve 8.468 mmol of (N-cyclohexylaminomethyl)triethoxysilane (Gelest, Inc.), then 8.468 mmol of ethylene glycol methyl ether acrylate (Acros Organics) was added thereto, and the result was stirred for 8 hours at room temperature under nitrogen atmosphere. After the reaction was complete, the solvent was removed under vacuum, and the result was vacuum distilled at 120° C. to obtain 8.19 mmol of 2-methoxyethyl 3-(cyclohexyl((triethoxysilyl)methyl)amino)propanoate (iii) (yield 96.7%). 1H Nuclear Magnetic Resonance spectroscopic data of the purified 2-methoxyethyl 3-(cyclohexyl((triethoxysilyl)methyl)amino)propanoate are as follows.

the result was vacuum distilled at 120° C. to obtain 6.24 mmol of 2-(dimethylamino)ethyl 3-(cyclohexyl((triethoxysilyl)methyl)amino)propanoate (iv) (yield 94.8%). 1H Nuclear Magnetic Resonance spectroscopic data of the purified 2-(dimethylamino)ethyl 3-(cyclohexyl((triethoxysilyl)methyl)amino)propanoate are as follows.

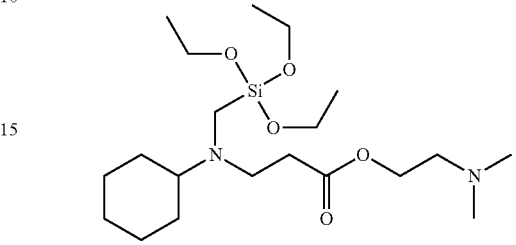

(iv)

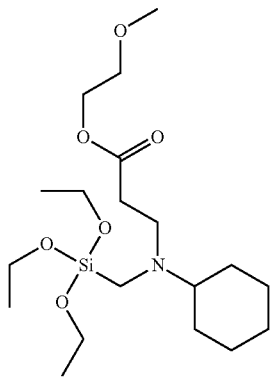

(iii)

$^1$H-NMR (500 MHz, CDCl$_3$) δ 4.18-4.16 (t, 2H), δ 3.84-3.79 (m, 3H), δ3.55-3.54 (t, 2H), δ 3.35 (s, 3H), δ 2.76-2.73 (m, 2H), δ 2.48-2.45 (m, 4H), δ2.14-2.08 (m, 3H), δ 1.73-1.71 (m, 7H), δ 1.22-1.18 (m, 13H)

$^1$H-NMR (500 MHz, CDCl$_3$) δ 4.16-4.08 (m, 3H), δ 2.76-2.73 (m, 2H), δ2.53-2.50 (m, 3H), δ 2.47-2.41 (m, 3H), δ 2.25-2.23 (m, 10H), δ 2.11-2.08 (t, 2H), δ 1.73-1.72 (m, 9H), δ 1.54-1.47 (m, 4H), δ 1.24-1.16 (m, 10H)

PREPARATION EXAMPLE 4

Preparation of 2-(dimethylamino)ethyl 3-(cyclohexyl((triethoxysilyl)methyl)amino)propanoate In a 50 ml round bottom flask, 5 ml of ethanol was added to dissolve 6.586 mmol of (N-cyclohexylaminomethyl)triethoxysilane (Gelest, Inc.), then 6.586 mmol of 2-(dimethylamino)ethyl acrylate (Sigma-Aldrich Co. LLC.) was added thereto, and the result was stirried for 8 hours at room temperature under nitrogen atmosphere. After the reaction was complete, the solvent was removed under vacuum, and

PREPARATION EXAMPLE 5

Preparation of 2,5,8,11,14,17,20,23,26-nonaoxaoctacosan-28-yl 3-(bis(3-(triethoxysily)propyl)amino)propanoate In a 50 ml round bottom flask, 5 ml of ethanol was added to dissolve 2.279 mmol of bis(3-triethoxysilylpropyl)amine (Gelest, Inc.), then 2.279 mmol of poly(ethylene glycol) methyl ether acrylate (Sigma-Aldrich Co. LLC., Mn 480) was added thereto, and the result was stirried for 8 hours at room temperature under nitrogen atmosphere. After the reaction was complete, the solvent was removed under vacuum, and the result was vacuum distilled at 120° C. to obtain 2.13 mmol of 2,5,8,11,14,17,20,23,26-nonaoxaoctacosan-28-yl 3-(bis(3-(triethoxysilyl)propyl)amino)propanoate (v) (yield 93.5%). 1H Nuclear Magnetic Resonance spectroscopic data of the purified 2,5,8,11,14,17,20,23,26-nonaoxaoctacosan-28-yl 3-(bis(3-(triethoxysilyl)propyl)amino)propanoate are as follows.

(v)

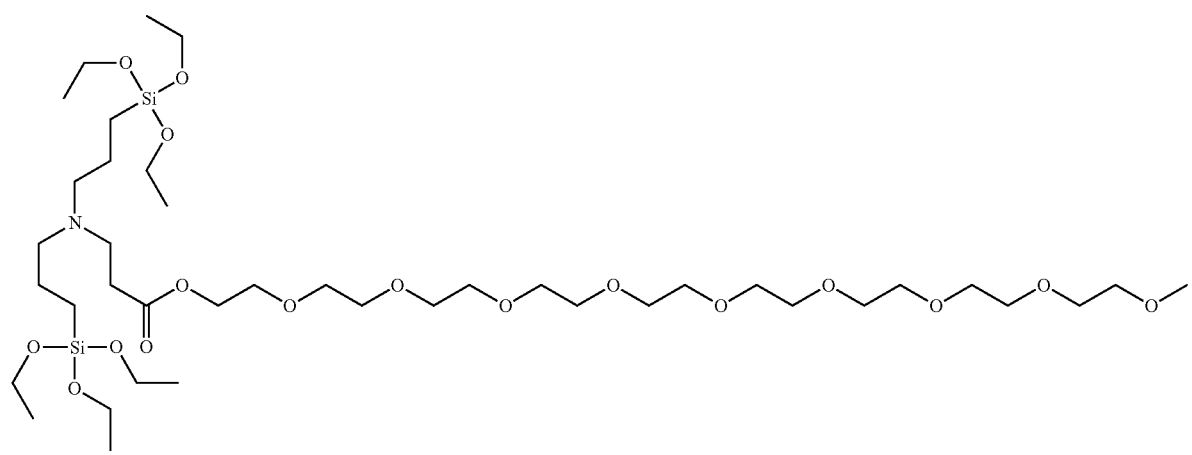

¹H-NMR (500 MHz, CDCl₃) δ 4.17-4.15 (t, 2H), δ 3.78-3.73 (m, 12H), δ 3.60-3.59 (m, 32H), δ 3.50-3.48 (m, 2H), δ 3.32 (s, 3H), δ 2.74-2.71 (m, 2H), δ 2.37-2.34 (t, 6H), δ 1.50-1.43 (m, 4H), δ 1.19-1.15 (t, 18H), δ 0.54-0.50 (m, 4H)

PREPARATION EXAMPLE 6

Preparation of 2-(2-(2-(2-phenoxyethoxy)ethoxy)ethoxy)ethyl 3-(bis(3-(triethoxysilyl)propyl) amino)propanoate In a 50 ml round bottom flask, 5 ml of ethanol was added to dissolve 2.279 mmol of bis(3-triethoxysilylpropyl)amine, then 2.279 mmol of poly(ethylene glycol) phenyl ether acrylate (Sigma-Aldrich, Co. LLC. Mn 324) was added thereto, and the result was stirried for 8 hours at room temperature under nitrogen atmosphere. After the reaction was complete, the solvent was removed under vacuum, and the result was vacuum distilled at 120° C. to obtain 2.15 mmol of 2-(2-(2-(2-phenoxyethoxy)ethoxy)ethoxy)ethyl 3-(bis(3-(triethoxysilyl)propyl)amino)propanoate (vi) (yield 93.7%). 1H Nuclear Magnetic Resonance spectroscopic data of the purified 2-(2-(2-(2-phenoxyethoxy)ethoxy)ethoxy)ethyl 3-(bis(3-(triethoxysilyl)propyl)amino)propanoate are as follows.

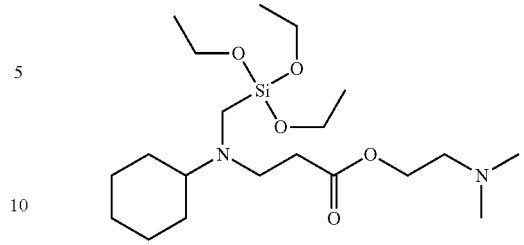

(vii)

¹H-NMR (500 MHz, CDCl₃) δ 7.26-7.23 (m, 2H), δ 6.94-6.84 (m, 3H), δ 4.39-4.37 (t, 2H), δ 4.14-4.12 (t, 3H), δ 3.79-3.75 (m, 12H), δ 2.78-2.75 (t,2H), δ 2.46-2.43 (t, 2H), δ 2.39-2.36 (t, 4H), δ 1.63-1.43 (m, 4H), δ 1.20-1.17 (m, 18H), δ 0.56-0.52 (m, 4H)

PREPARATION EXAMPLE 8

Preparation of 2-methoxyethyl 3-(bis(3-(triethoxysilyl)propyl)amino)propanoate

In a 50 ml round bottom flask, 5 ml of ethanol was added to dissolve 4.557 mmol of bis(3-triethoxysilylpropyl)amine

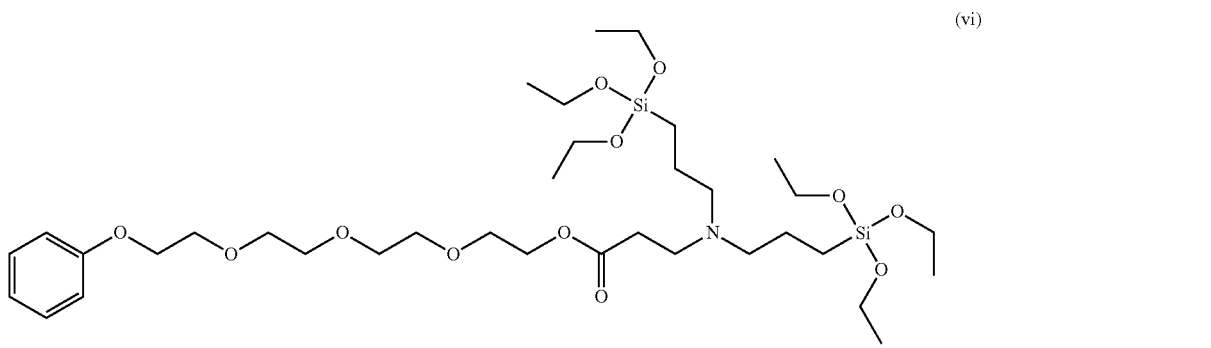 [SMILES: CCO[Si](CCCN(CCC[Si](OCC)(OCC)OCC)CCC(=O)OCCOCCOCCOCCOc1ccccc1)(OCC)OCC]

(vi)

¹H-NMR (500 MHz, CDCl₃) δ 7.26-7.22 (t, 2H), δ 6.92-6.87 (m, 3H), δ 4.20-4.17 (t, 2H), δ 4.11-4.07 (m, 3H), δ 3.84-3.82 (m, 2H), δ 3.81-3.75 (m, 10H), δ 3.71-3.60 (m, 10H), δ 2.77-2.74 (t, 2H), δ 2.39-2.36 (t, 6H), δ 1.52-1.46 (m, 4H), δ 1.21-1.78 (m, 18H), δ 0.57-0.53 (m, 4H)

PREPARATION EXAMPLE 7

Preparation of 2-phenoxyethyl 3-(bis(3-(triethoxysilyl)propyl)amino)propanoate

In a 50 ml round bottom flask, 5 ml of ethanol was added to dissolve 4.557 mmol of bis(3-triethoxysilylpropyl)amine (Gelest, Inc.), then 4.557 mmol of 2-phenoxyethyl acrylate (TCI Co., Ltd.) was added thereto, and the result was stirried for 8 hours at room temperature under nitrogen atmosphere. After the reaction was complete, the solvent was removed under vacuum, and the result was vacuum distilled at 120° C. to obtain 4.17 mmol of 2-phenoxyethyl 3-(bis(3-(triethoxysilyl)propyl)amino)propanoate (vii) (yield 91.6%). 1H Nuclear Magnetic Resonance spectroscopic data of the purified 2-phenoxyethyl 3-(bis(3-(triethoxysilyl)propyl)amino)propanoate are as follows.

(Gelest, Inc.), then 4.557 mmol of ethylene glycol methyl ether acrylate (Acros Organics) was added thereto, and the result was stirried for 8 hours at room temperature under nitrogen atmosphere. After the reaction was complete, the solvent was removed under vacuum, and the result was vacuum distilled at 120° C. to obtain 4.430 mmol of 2-methoxyethyl 3-(bis(3-(triethoxysilyl)propyl)amino)propanoate (i) (yield 97.3%). 1H Nuclear Magnetic Resonance spectroscopic data of the purified 2-methoxyethyl 3-(bis(3-(triethoxysilyl)propyl)amino)propanoate are as follows.

¹H-NMR (500 MHz, CDCl₃) δ 4.21-4.19 (t, 2H), δ 3.81-3.77 (m, 12H), δ 3.57-3.56 (t, 2H), δ 3.36 (s, 3H), δ 2.79-2.76 (t, 2H), δ 2.47-2.44 (t, 2H), δ 2.40-2.37 (t, 4H), δ 1.54-1.47 (m, 4H), δ 1.22-1.19 (t, 18H), δ 0.57-0.54 (t, 4H)

PREPARATION EXAMPLE 9

Preparation of 2-(dimethylamino)ethyl 3-(bis(3-(triethoxysilyl)propyl)amino)propanoate In a 50 ml round bottom flask, 5 ml of ethanol was added to dissolve 4.5573 mmol of bis(3-triethoxysilylpropyl)amine (Gelest, Inc.), then 4.55764 mmol of 2-(dimethylamino)ethyl acrylate (Sigma-Aldrich Co. LLC.) was added thereto, and the result was stirred for 8 hours at room temperature under nitrogen atmosphere. After the reaction was complete, the solvent was removed under vacuum, and the result was vacuum distilled at 120° C. to obtain 4.18 mmol of 2-(dimethylamino)ethyl 3-(bis(3-(triethoxysilyl)propyl)amino)propanoate (viii) (yield 91.7%). 1H Nuclear Magnetic Resonance spectroscopic data of the purified 2-(dimethylamino)ethyl 3-(bis(3-(triethoxysilyl)propyl)amino)propanoate are as follows.

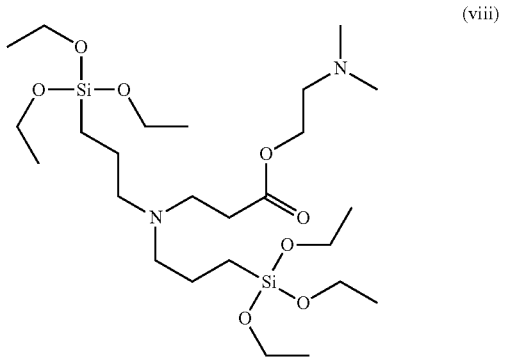 [SMILES: CCO[Si](CCCN(CCC[Si](OCC)(OCC)OCC)CCC(=O)OCCN(C)C)(OCC)OCC]

(viii)

$^1$H-NMR (500 MHz, CDCl$_3$) δ 4.12-4.09 (t, 2H), δ 3.78-3.74 (m, 12H), δ 2.75-2.73 (t, 2H), δ 2.51-2.49 (t, 3H), δ 2.42-2.40 (t, 2H), δ 2.37-2.34 (t, 3H), δ 2.22-2.19 (m, 6H), δ 1.54-1.44 (m, 4H), δ 1.18-1.15 (m, 18H), δ 0.52-0.50 (m, 4H)

PREPARATION EXAMPLE 10

Preparation of 2-(2-(2-(2-phenoxyethoxy)ethoxy)ethoxy)ethyl 3-(cyclohexyl((triethoxysilyl)methyl)amino)propanoate In a 50 ml round bottom flask, 50 ml of ethanol was added to dissolve 3.449 mmol of (N-cyclohexylaminomethyl)triethoxysilane, then 3.449 mmol of poly(ethylene glycol) phenylether acrylate (Sigma-Aldrich Co. LLC., Mn 324) was added thereto, and the result was stirred for 8 hours at room temperature under nitrogen atmosphere. After the reaction was complete, the solvent was removed under vacuum, and the result was vacuum distilled at 120° C. to obtain 3.13 mmol of 2-(2-(2-(2-phenoxyethoxy)ethoxy)ethoxy)ethyl 3-(cyclohexyl((triethoxysilyl)methyl)amino)propanoate (ix) (yield 91.1%). 1H Nuclear Magnetic Resonance spectroscopic data of the purified 2-(2-(2-(2-phenoxyethoxy)ethoxy)ethoxy)ethyl 3-(cyclohexyl((triethoxysilyl)methyl)amino)propanoate are as follows.

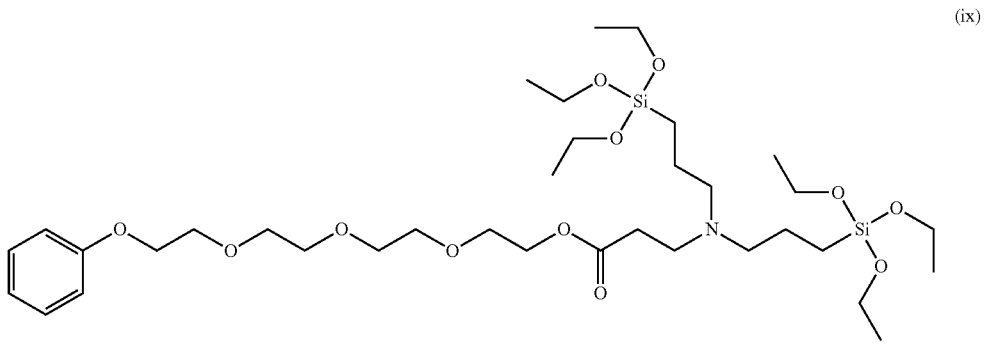 [SMILES: CCO[Si](CCCN(CCC[Si](OCC)(OCC)OCC)CCC(=O)OCCOCCOCCOCCOc1ccccc1)(OCC)OCC]

(ix)

$^1$H-NMR (500 MHz, CDCl$_3$) δ 7.26-7.24 (m, 2H), δ 6.93-6.88 (m, 3H), δ 4.18-4.16 (m, 2H), δ 4.11-4.09 (m, 3H), δ 3.85-3.80 (m, 6H), δ 3.71-3.61 (m, 12H), δ 2.76-2.72 (m, 2H), δ 2.50-2.39 (m, 3H), δ 2.10-2.09 (m, 2H), δ 1.74-1.72 (m, 4H), δ 1.58-1.59 (m, 1H) δ 1.24-1.15 (m, 12H), δ 1.03-1.00 (m, 1H)

PREPARATION EXAMPLE 11

Preparation of 2-methoxyethyl 3-(bis(3-(diethoxy(methyl)silyl)propyl)amino)propanoate In a 100 ml round bottom flask, 20 ml of ethanol was added to dissolve 73.03 mmol of bis(methyldiethoxysilylpropyl)amine (Gelest, Inc.), then 73.03 mmol of ethylene glycol methyl ether acrylate (Acros Organics) was added thereto, and the result was stirred for 8 hours at room temperature under nitrogen atmosphere. After the reaction was complete, the solvent was removed under vacuum, and the result was vacuum distilled at 120° C. to obtain 71.77 mmol of 2-methoxyethyl 3-(bis(3-(diethoxy(methyl)silyl)propyl)amino)propanoate (x) (yield 98.327%). 1H Nuclear Magnetic Resonance spectroscopic data of the purified 2-methoxyethyl 3-(bis(3-(diethoxy(methyl)silyl)propyl)amino)propanoate are as follows.

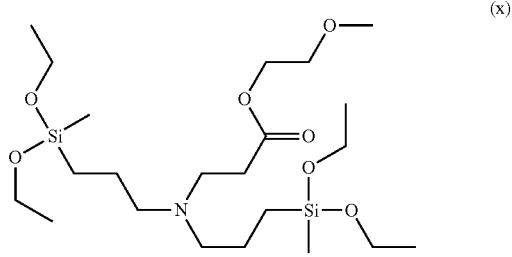 [SMILES: CCO[Si](C)(CCCN(CCC[Si](C)(OCC)OCC)CCC(=O)OCCOC)OCC]

(x)

$^1$H-NMR (500 MHz, CDCl$_3$) δ 4.23-4.21 (t, 2H), δ 3.78-3.74 (m, 8H), δ 3.60-3.58 (t, 2H), δ 3.39 (s, 3H), δ 2.81-2.78 (t, 2H), δ 2.49-2.46 (t, 2H), δ 2.42-2.39 (t, 3H), δ 1.51-1.45 (m, 5H), δ 1.23-1.20 (t, 18H), δ 0.57-0.54 (t, 4H), δ 0.12 (s, 6H)

PREPARATION EXAMPLE 12

Preparation of ethyl 3-(bis(3-(diethoxy(methyl)silyl)propyl)amino)propanoate

In a 100 ml round bottom flask, 20 ml of ethanol was added to dissolve 72.99 mmol of bis(methyldiethoxysilylpropyl)amine (Gelest, Inc.), then 72.99 mmol of ethyl acrylate (Sigma-Aldrich Co. LLC.) was added thereto, and the result was stirried for 8 hours at room temperature under nitrogen atmosphere. After the reaction was complete, the solvent was removed under vacuum, and the result was vacuum distilled at 80° C. to obtain 72.18 mmol of ethyl 3-(bis(3-(diethyoxy(methyl)silyl)propyl)amino)propanoate (xi) (yield 98.9%). 1H Nuclear Magnetic Resonance spectroscopic data of the purified ethyl 3-(bis(3-(diethoxy(methyl)silyl)propyl)amino)propanoate are as follows.

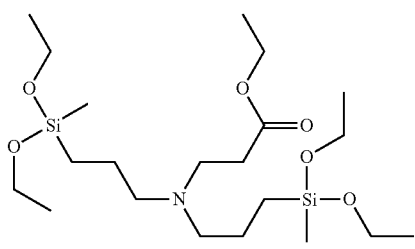

(xi)

$^1$H-NMR (500 MHz, CDCl$_3$) δ 4.14-4.10 (m, 2H), δ 3.78-3.74 (m, 8H), δ2.80-2.79 (t, 2H), δ 2.43-2.39 (m, 6H), δ 1.52-1.54 (m, 4H), δ 1.27-1.20 (m, 15H), δ 0.58-0.54 (t, 4H), δ 0.11 (s, 6H)

EXAMPLE 1-1

Preparation of Modified Butadiene Polymer

Under nitrogen atmosphere, 4.2 kg of hexane and 500 g of 1,3-butadiene were placed in a 15 L reactor, and the temperature was raised to 70° C. A catalyst for polymerization prepared through a reaction of 1.0 mmol of neodymium versatate (NdV) hexane solution, 9.2 mmol of diisobutylaluminum hydride (DIBAH), 2.4 mmol of diethylaluminum chloride and 33 mmol of 1,3-butadiene was added to the 15 L reactor, and the result was polymerized for 60 minutes. A conversion rate of the 1,3-butadiene to polybutadiene was approximately 100%.

After completing the polymerization reaction of the 1,3-butadiene, a hexane solution including 7.0 mmol of an aminosilane-based modifier was added to the above polymerized solution, and the result was reacted for 30 minutes at 70° C. Through the addition of a hexane solution including 1.0 g of a reaction terminating agent and a hexane solution including 1.0 g of an antioxidant, a modified butadiene polymer was prepared.

EXAMPLES 1-2 to 1-12

Preparation of Modified Butadiene Polymer

Modified butadiene polymers were prepared in the same manner as in Example 1-1 except that the modifiers prepared in Preparation Examples 2 to 12 were each used as the modifier in Example 1-1.

EXAMPLES 1-13

Preparation of Modified Butadiene Polymer

A modified butadiene polymer was prepared in the same manner as in Example 1-1 except that Nd(2,2-dihexyl decanoate)$_3$ (xii) of the following structure was used instead of the neodymium versatate in the 1,3-butadiene polymerization reaction in Example 1-1.

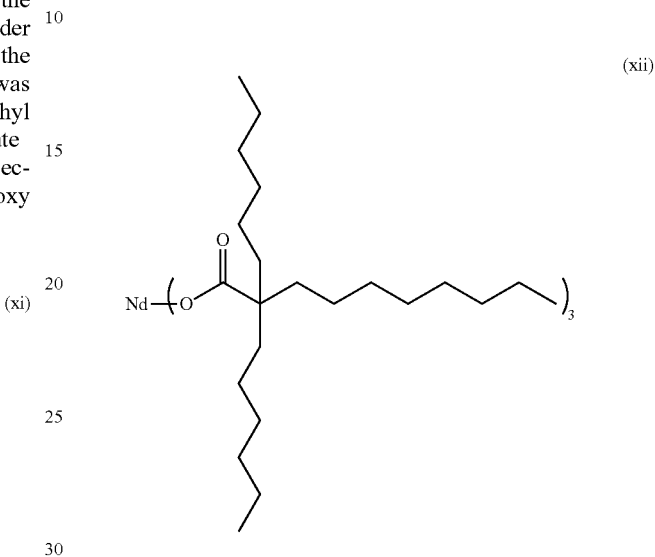

(xii)

EXAMPLES 1-14 to 1-24

Preparation of Modified Butadiene Polymer

Modified butadiene polymers were prepared in the same manner as in Example 1-1 except that Nd(2,2-dihexyl decanoate)$_3$ was used instead of the neodymium versatate in the 1,3-butadiene polymerization reaction, and the modifiers prepared in Preparation Examples 2 to 12 were each used instead of the modifier in Example 1-1.

COMPARATIVE EXAMPLE 1-1

As non-modified ND-BR, Nd60™ (manufactured by Kumho Petrochemical) was used.

COMPARATIVE EXAMPLE 1-2

As modified ND-BR, BR54™ (manufactured by JSR Corporation) was used.

COMPARATIVE EXAMPLE 1-3

Preparation of Butadiene Polymer

A butadiene polymer was prepared in the same manner as in Example 1-1 except that no modifier was used.

COMPARATIVE EXAMPLE 1-4

Preparation of Modified Butadiene Polymer

A modified butadiene polymer was prepared in the same manner as in Example 1-1 except that 3-glycidoxypropyltrimethoxysilane (GPMOS) (xiii) of the following structure was used as the modifier.

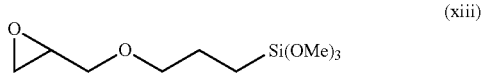

(xiii)

Test Example 1

For the polymers prepared in Example 1-1, 1-13 and Comparative Examples 1-1 to 1-4, the modification status, the weight average molecular weight (Mw), the number average molecular weight (Mn), the molecular weight distribution (MWD), and the Mooney viscosity (MV) were each measured as follows.

Weight average molecular weight (Mw), number average molecular weight (Mn) and molecular weight distribution (MWD): measured using gel permeation chromatography for the polymers prepared in Example 1-1 and Comparative Examples 1-1 to 1-4.

Mooney viscosity (MV) (ML1+4, @100° C.) (MU): measured using a Large Rotor of MV2000E manufactured by Monsanto under a condition of Rotor Speed 2±0.02 rpm at 100° C. Herein, the used sample was left unattended for 30 minutes or longer at room temperature (23±3° C.), 27±3 g thereof was collected, and inside a die cavity is filled with the sample, and Mooney viscosity was measured while operating a Platen.

EXAMPLE 2-1

Preparation of Rubber Composition

A rubber composition was prepared by mixing butadiene rubber in 100 parts by weight, silica in 70 parts by weight, bis(3-triethoxysilylpropyl)tetrasulfide in 6 parts by weight as a silane coupling agent, process oil in 30 parts by weight, an antiaging agent (TMDQ) in 4 parts by weight, zinc oxide (ZnO) in 3 parts by weight and stearic acid in 2 parts by weight, with respect to 100 parts by weight of the modified butadiene-based polymer prepared in Example 1-1. To the prepared rubber composition, 2 parts by weight of sulfur powder, 2 parts by weight of a vulcanization accelerator (CZ) and 2 parts by weight of a vulcanization accelerator (DPG) were added, and the result was vulcanized for t90 minutes at 150° C. to prepare a rubber specimen. Herein, as the silica, silica having a nitrogen adsorption specific surface area of 175 $m^2/g$ and a CTAB adsorption value of 160 $m^2/g$ was used.

EXAMPLES 2-2 to 2-24

Preparation of Rubber Composition

Rubber compositions were prepared in the same manner as in Example 2-1 except that each of the modified butadi-

TABLE 1

| | | Comparative Example 1-1 | Comparative Example 1-2 | Comparative Example 1-3 | Comparative Example 1-4 | Example 1-1 | Example 1-13 |
|---|---|---|---|---|---|---|---|
| Type of Modifier | | Nd60 ™ (Kumho Petrochemical) [1] | BR54 ™ (JSR Corporation) [2] | — | GPMOS | Compound (i) | Compound (i) |
| Modification Status | | Non-modified | Modified | Non-modified | Modified | Modified | Modified |
| GPC Result | Mn (×$10^5$ g/mol) | 2.56 | N/A (gel formed) | 3.03 | 2.99 | 3.00 | 3.15 |
| | Mw (×$10^5$ g/mol) | 8.99 | | 9.45 | 10.31 | 9.57 | 9.52 |
| | Mw/Mn | 3.51 | | 3.11 | 3.45 | 3.18 | 3.02 |
| MV (ML1 + 4, @100° C.) (MU) | | 62.9 | 69.9 | 59.8 | 64.7 | 62.8 | 61.9 |

In Table 1, 1) and 2) are polymers, N/A means unmeasurable.

In the test results, weight average, number average molecular weights and molecular weight distribution measured by GPC were difficult to be measured for the butadiene polymer of Comparative Example 1-2 using an existing modifier due to gelation.

Meanwhile, the modified butadiene-based polymers of Examples 1-1 and 1-13 modified using the modifiers according to the present invention exhibited narrower molecular weight distribution (Mw/Mn) compared to the modified butadiene-based polymer of Comparative Example 1-4 prepared using GPMOS as the modifier, and the modified butadiene-based polymer of Example 1-13 prepared using Nd(2,2-dihexyl decanoate)$_3$ as the Nd-based catalyst exhibited far narrower molecular weight distribution. From such a test result, it may be predicted that a modified butadiene copolymer using the modifier according to the present invention is capable of exhibiting improved effects in terms of viscoelasticity and a tensile property in a balanced way.

ene-based polymers prepared in Examples 1-2 to 1-24 was used instead of the modified butadiene-based polymer of Example 1-1.

COMPARATIVE EXAMPLES 2-1 to 2-4

Preparation of Rubber Composition

Rubber compositions were prepared in the same manner as in Example 2-1 except that the polymers prepared in Comparative Examples 1-1 to 1-4 were used instead of the modified butadiene-based polymer prepared in Example 1-1.

Test Example 2

For the rubber compositions of Examples 2-1 and 2-13 and Comparative Examples 2-1 to 2-4, a vulcanizing property and tensile properties were evaluated.

In detail, for the prepared rubber compositions, a vulcanizing property, viscoelasticity, and tensile properties including hardness, 300% modulus, tensile strength, elongation and toughness strength were each measured. Among these, viscoelasticity, 300% modulus, tensile strength, elongation and toughness strength were indexed with the measurement value of Comparative Example 3 as 100. The results are shown in the following Table 2.

Vulcanizing property (t90): maximum torque (MH) value and time taken for 90% vulcanization (t90) were measured when vulcanized for 50 minutes at 150° C. using a moving die rheometer (MDR).

Viscoelasticity (tan δ@60° C.): viscoelasticity coefficient (tan δ) at 60° C. was measured with 10 Hz frequency and 3% strain rate.

Hardness (Type A): type A harness was measured in accordance with the ASTM D2240.

Tensile strength (kg·f/cm²), 300% modulus (kg·f/cm²), elongation (%): each of the rubber compositions was vulcanized for t90 minutes at 150° C., and tensile strength of the vulcanized material, modulus at 300% elongation, and elongation of the vulcanized material when fractured were measured in accordance with the ASTM D412.

Toughness: area under the tensile graph when fractured was measured.

TABLE 2

|  |  | Comparative Example 2-1 | Comparative Example 2-2 | Comparative Example 2-3 | Comparative Example 2-4 | Example 2-1 | Example 2-13 |
|---|---|---|---|---|---|---|---|
| Type of Polymer |  | Comparative Example 1-1 | Comparative Example 1-2 | Comparative Example 1-3 | Comparative Example 1-4 | Example 1-1 | Example 1-13 |
| Vulcanizing Property | t90 (minutes) | 12.16 | 12.28 | 11.45 | 11.71 | 10.09 | 10.01 |
| Viscoelasticity (DMTS, 10 Hz) 3% strain | tanδ @60° C. | 92 | 97 | 100 | 109 | 112 | 117 |
| Tensile Property | Hardness (Type A) | 61 | 59 | 61 | 62 | 62 | 62 |
|  | 300% Modulus (Kg · f/cm²) | 98 | 98 | 100 | 110 | 122 | 128 |
|  | Tensile Strength (Kg · f/cm²) | 95 | 97 | 100 | 110 | 115 | 118 |
|  | Elongation (%) | 98 | 98 | 100 | 102 | 102 | 102 |
|  | Toughness (Kg · f/cm²) | 92 | 95 | 100 | 114 | 125 | 129 |

The rubber compositions of Example 2-1 including the modified butadiene-based polymer of Example 1-1; and Example 2-13 including the modified butadiene-based polymer of Example 1-13, both modified using the modifier according to the present invention, exhibited significantly improved effects compared to the rubber compositions including Comparative Examples 1-1 and 1-3, which are non-modified butadiene-based polymers, and Comparative Examples 1-2 and 1-4 using existing modifiers. From the above, it was seen that the rubber composition including the modified butadiene-based polymer of Example 1-1 exhibited more excellent fuel efficiency properties.

In addition, in the hardness property among the tensile properties, the rubber compositions including the polymers of Comparative Examples 1-1 to 1-4, or Example 1-1 and Example 1-13 exhibited an equal level of hardness regardless of modification. However, in 300% modulus, tensile strength, elongation and a toughness property, the rubber compositions including the modified butadiene copolymers of Example 1-1 and Example 1-13 exhibited significantly improved effects compared to the rubber compositions including Comparative Examples 1 and 3, which are non-modified butadiene-based polymers, and Comparative Examples 2-2 and 2-4 using existing modifiers.

What is claimed is:

1. A modified butadiene-based polymer as a modified polymer of a lanthanide rare earth element-catalyzed butadiene-based polymer, the polymer comprising:
   a modifier-derived functional group of the following Chemical Formula 1:

[Chemical Formula 1]

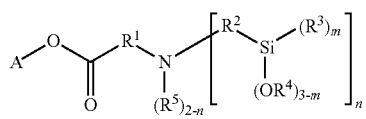

wherein, in Chemical Formula 1,
A is a hydrocarbon group having 1 to 20 carbon atoms, or a hydrocarbon group having 1 to 20 carbon atoms including one or more heteroatoms selected from the group consisting of N, S and O;
$R^1$ and $R^2$ are each independently a divalent hydrocarbon group having 1 to 20 carbon atoms unsubstituted or substituted with one or more substituents selected from the group consisting of a linear or branched alkyl group having 1 to 20 carbon atoms, a cycloalkyl group having 3 to 20 carbon atoms and an aryl group having 6 to 30 carbon atoms;
$R^3$ to $R^5$ are each independently a monovalent hydrocarbon group having 1 to 20 carbon atoms;
m is an integer of 0 to 3; and
n is an integer of 1 or 2, but when A is the hydrocarbon group having 1 to 20 carbon atoms, n is an integer of 2.

2. The modified butadiene-based polymer of claim 1, wherein, in Chemical Formula 1, A is selected from the group consisting of an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkoxy group having 1 to 20 carbon atoms, an alkoxyalkyl group having 2 to 20 carbon atoms, a phenoxyalkyl group having 7 to 20 carbon atoms, an aminoalkyl group having 1 to 20 carbon atoms and -[R$^{11}$O]$_x$R$^{12}$, wherein, R$^{11}$ is an alkylene group having 2 to 10 carbon atoms, R$^{12}$ is selected from the group consisting of a hydrogen atom, an alkyl group having 1 to 10 carbon atoms, a cycloalkyl group having 3 to 12 carbon atoms, an aryl group having 6 to 16 carbon atoms and an arylalkyl group having 7 to 16 carbon atoms, and x is an integer of 2 to 10.

3. The modified butadiene-based polymer of claim 1, wherein, in Chemical Formula 1, A is any one selected from the group consisting of an alkyl group having 1 to 10 carbon atoms, a cycloalkyl group having 3 to 12 carbon atoms, an aryl group having 6 to 12 carbon atoms, an arylalkyl group having 7 to 12 carbon atoms, an alkoxyalkyl group having 2 to 10 carbon atoms, a phenoxyalkyl group having 7 to 12 carbon atoms, an aminoalkyl group having 1 to 10 carbon atoms and -[R$^{11}$O]$_x$R$^{12}$, wherein, R$^{11}$ is an alkylene group having 2 to 10 carbon atoms, R$^{12}$ is selected from the group consisting of a hydrogen atom, an alkyl group having 1 to 10 carbon atoms, a cycloalkyl group having 3 to 12 carbon atoms, an aryl group having 6 to 16 carbon atoms and an arylalkyl group having 7 to 16 carbon atoms, and x is an integer of 2 to 10;
R$^1$ and R$^2$ are each independently an alkylene group having 1 to 5 carbon atoms;
R$^3$ and R$^4$ are each independently an alkyl group having 1 to 5 carbon atoms;
R$^5$ is an alkyl group having 1 to 5 carbon atoms or a cycloalkyl group having 3 to 8 carbon atoms;
m is an integer of 0 to 2; and
n is an integer of 1 or 2, but when A is the alkyl group having 1 to 10 carbon atoms, the cycloalkyl group having 3 to 12 carbon atoms, the aryl group having 6 to 12 carbon atoms or the arylalkyl group having 7 to 12 carbon atoms, n is an integer of 2.

4. The modified butadiene-based polymer of claim 1, wherein the modifier includes any one or a mixture of two or more selected from the group consisting of 2-methoxyethyl 3-(bis(3-(triethoxysilyl)propyl)amino)propanoate, 2-phenoxyethyl 3-(bis(3-(triethoxysilyl)propyl)amino)propanoate, 2-methoxyethyl 3-(bis(3-(diethoxy(methyl)silyl) propyl)amino)propanoate, 2-ethoxyethyl 3-(bis(3-(diethoxy(methyl)silyl)propyl)amino)propanoate, ethyl 3 -(bis(3-(diethoxy(methyl)silyl)propyl)amino)propanoate, 2-phenoxyethyl 3-(cyclohexyl((triethoxysilyl)methyl) amino)propanoate, 2-methoxyethyl 3-(cyclohexyl((triethoxysilyl)methyl)amino)propanoate, 2-(dimethylamino)ethyl 3-(cyclohexyl((triethoxysilyl)methyl)amino)propanoate, 2,5,8,11,14,17,20,23,26-nonaoxaoctacosan-28-yl 3-(bis(3-(triethoxysilyl)propyl)amino)propanoate, 2-(2-(2-(2-phenoxyethoxy)ethoxy)ethoxy)ethyl 3-(bis(3-(triethoxysilyl) propyl)amino)propanoate, 2-(dimethylamino)ethyl 3-(bis(3-(triethoxysilyl)propyl)amino)propanoate, 2-(2-(2-(2-phenoxyethoxy)ethoxy)ethoxy)ethyl 3-(bis(3-(cyclohexyl (triethoxy)lsilyl)methyl)amino)propanoate,2-methoxyethyl 3-(bis(3-(diethoxy(methyl)silyl)propyl)amino)propanoate and ethyl 3-(bis(3-(diethoxy(methyl)silyl)propyl)amino) propanoate.

5. The modified butadiene-based polymer of claim 1, wherein A is any one selected from the group consisting of an alkyl group having 1 to 10 carbon atoms, an alkoxyalkyl group having 2 to 10 carbon atoms and a phenoxyalkyl group having 7 to 12 carbon atoms;

R$^1$ and R$^2$ are each independently an alkylene group having 1 to 5 carbon atoms;
R$^3$ and R$^4$ are each independently an alkyl group having 1 to 5 carbon atoms;
m is an integer of 0 or 1; and
n is an integer of 2.

6. The modified butadiene-based polymer of claim 1, which is prepared by modifying a butadiene-based polymer having an active organic metal site obtained by polymerizing a butadiene-based monomer using a catalyst including a lanthanide rare earth element-containing compound with the modifier.

7. The modified butadiene-based polymer of claim 6, wherein the butadiene-based polymer having an active organic metal site is a neodymium-catalyzed butadiene-based polymer including a 1,3-butadiene monomer-derived repeating unit.

8. The modified butadiene-based polymer of claim 1, which has molecular weight distribution (Mw/Mn) of 2.5 to 3.5.

9. The modified butadiene-based polymer of claim 1, which has a weight average molecular weight of 5×10$^5$ g/mol to 1.2×10$^6$ g/mol, and a number average molecular weight of 1.5×10$^5$ g/mol to 3.5×10$^5$ g/mol.

10. The modified butadiene-based polymer of claim 1, which has Mooney viscosity of 40 to 70 at 100° C.

11. A method for preparing the modified butadiene-based polymer of claim 1 comprising:
modifying by reacting a butadiene-based polymer having a lanthanide rare earth element-catalyzed active organic metal site with a modifier of the following Chemical Formula 1:

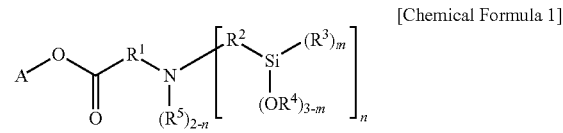

[Chemical Formula 1]

wherein, in Chemical Formula 1,
A is a hydrocarbon group having 1 to 20 carbon atoms, or a hydrocarbon group having 1 to 20 carbon atoms including one or more heteroatoms selected from the group consisting of N, S and O;
R$^1$ and R$^2$ are each independently a divalent hydrocarbon group having 1 to 20 carbon atoms unsubstituted or substituted with one or more substituents selected from the group consisting of a linear or branched alkyl group having 1 to 20 carbon atoms, a cycloalkyl group having 3 to 20 carbon atoms and an aryl group having 6 to 30 carbon atoms;
R$^3$ to R$^5$ are each independently a monovalent hydrocarbon group having 1 to 20 carbon atoms;
m is an integer of 0 to 3; and
n is an integer of 1 or 2, but when A is the hydrocarbon group having 1 to 20 carbon atoms, n is an integer of 2.

12. The method for preparing the modified butadiene-based polymer of claim 11, further comprising:
preparing the butadiene-based polymer having an active organic metal site by polymerizing a butadiene-based monomer in an organic solvent using a catalyst for polymerization including a lanthanide rare earth element-containing compound prior to the modifying.

13. The method for preparing the modified butadiene-based polymer of claim 12, wherein the catalyst for polymerization includes a lanthanide rare earth element-containing compound, an alkylating agent and a halogen compound.

14. The method for preparing the modified butadiene-based polymer of claim 12, wherein the lanthanide rare earth element-containing compound includes a neodymium compound of the following Chemical Formula 4:

[Chemical Formula 4]

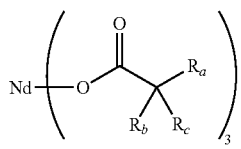

wherein, in Chemical Formula 4, $R_a$ to $R_c$, are each independently a hydrogen atom, or a linear or branched alkyl group having 1 o 12 carbon atoms.

15. The method for preparing the modified butadiene-based polymer of claim 12, wherein the lanthanide rare earth element-containing compound includes a neodymium compound in which, in Chemical Formula 1, $R_a$ is a linear or branched alkyl group having 6 to 12 carbon atoms, and $R_b$, and $R_c$, are each independently a linear or branched alkyl group having 2 to 8 carbon atoms.

16. The method for preparing the modified butadiene-based polymer of claim 12, wherein the catalyst for polymerization further includes a diene-based monomer.

17. The method for preparing the modified butadiene-based polymer of claim 11, wherein the butadiene-based polymer having an active organic metal site is an end activated polymer.

18. The method for preparing the modified butadiene-based polymer of claim 11, wherein the butadiene-based polymer including an active organic metal site is a neodymium-catalyzed butadiene-based polymer including a 1,3-butadiene monomer-derived repeating unit.

19. The modified butadiene-based polymer of claim 1, wherein, in Chemical Formula 1, A is selected from the group consisting of an alkoxy group having 1 to 20 carbon atoms, an alkoxyalkyl group having 2 to 20 carbon atoms, a phenoxyalkyl group having 7 to 20 carbon atoms, an aminoalkyl group having 1 to 20 carbon atoms and $-[R^{11}O]_xR^{12}$, wherein, $R^{11}$ is an alkylene group having 2 to 10 carbon atoms, $R^{12}$ is selected from the group consisting of a hydrogen atom, an alkyl group having 1 to 10 carbon atoms, a cycloalkyl group having 3 to 12 carbon atoms, an aryl group having 6 to 16 carbon atoms and an arylalkyl group having 7 to 16 carbon atoms, and x is an integer of 2 to 10.

* * * * *